US006465516B1

(12) United States Patent
Kaesemeyer

(10) Patent No.: US 6,465,516 B1
(45) Date of Patent: Oct. 15, 2002

(54) METHOD OF STIMULATING NITRIC OXIDE SYNTHASE

(75) Inventor: Wayne H. Kaesemeyer, Augusta, GA (US)

(73) Assignee: Nitrosystems, Inc., Augusta, GA (US)

( * ) Notice: Subject to any disclaimer, the term of this patent is extended or adjusted under 35 U.S.C. 154(b) by 0 days.

(21) Appl. No.: 09/420,328

(22) Filed: Oct. 18, 1999

Related U.S. Application Data

(63) Continuation of application No. 08/833,842, filed on Apr. 10, 1997, now Pat. No. 5,968,983.

(51) Int. Cl.⁷ .................... A61K 31/22; A61K 31/351; A61K 31/405

(52) U.S. Cl. .................. 514/548; 514/419; 514/460

(58) Field of Search ................... 514/569, 565, 514/419, 460, 548

(56) References Cited

U.S. PATENT DOCUMENTS

| | | | |
|---|---|---|---|
| 4,444,784 A | 4/1984 | Hoffman et al. | 424/279 |
| 4,686,211 A | 8/1987 | Hara et al. | 514/148 |
| 5,059,712 A | 10/1991 | Griffith | 562/560 |
| 5,132,453 A | 7/1992 | Griffith | 562/560 |
| 5,158,883 A | 10/1992 | Griffith | 435/240.2 |
| 5,196,195 A | 3/1993 | Griffith | 424/94.6 |
| 5,270,323 A | 12/1993 | Milne, Jr. et al. | 514/309 |
| 5,316,765 A | 5/1994 | Folkers et al. | 424/94.1 |
| 5,428,070 A | 6/1995 | Cooke et al. | 514/557 |
| 5,543,430 A | 8/1996 | Kaesemeyer | 514/565 |
| 5,595,970 A | 1/1997 | Garfield et al. | 514/12 |
| 6,147,109 A | 1/2000 | Liao et al. | 514/460 |

FOREIGN PATENT DOCUMENTS

| | | |
|---|---|---|
| EP | 0 671 171 | 9/1995 |
| WO | WO 98/34626 | 8/1998 |
| WO | WO 98/44893 | 10/1998 |
| WO | 99/18952 | 4/1999 |
| WO | WO 99/47153 | 9/1999 |
| WO | WO 00/03746 | 1/2000 |
| WO | WO 00/40086 | 7/2000 |
| WO | WO 00/45809 | 8/2000 |
| WO | WO 00/56403 | 9/2000 |
| WO | WO 00/62614 | 10/2000 |

OTHER PUBLICATIONS

Otsuka et al., J. Hypertension (12, Suppl. 3. S108, 1994).*
Rubba et al., Current Opinion in Lipidology, 6:348–353 (1995).*
Egashira et al., Ann. N.Y. Acad. Sci., 748, 622–5, 1995 (abstract).*
Sunderkotter et al. Macrophages and angiogenesis. J. Leukoc. Biol. Mar. 1994, vol. 55, No. 3, pp. 410–420.
Bassenge, E. Coronary Vasomotor Responses: Role of Endothelium and Nitrovasodilators. Cardiovascular Drugs and Therapy. 1994, vol. 8, pp. 601–610.

O'Driscoll et al.: "the HMG–CoA reductase inhibitor simvastatin endothelial function within one month" Circulation, vol. 94, No. 8, 1996, pp. 1–401, XP002091894 (abstract).
Endres et al.: "stroke protection by HMG–CoA reductase inhibitors mediated by endothelial nitric oxide synthase" Proc Natl Acad Sci USA, vol. 95, No. 15, Jun. 21, 1998, pp. 8880–8885.
Endres et al.: "simvastatin pretreatment protects from focal cerebral ischema" Stroke, vol. 29, No. 1, Jan. 1998, p. 325.
Di Napoli et al.:"simvastatin exerts a direct anti–ischemic effect" Eur>Heart J., vol. 19, Aug. 1998, p. 124.
Laufs et al.:"inhibition of HMG–CoA reductase blocks hypoxia–mediated down–regulation of endothelial nitric oxide synthase" J Biol Chem, vol. 272, No. 50, Dec. 12, 1997, pp. 31725–31729.
Laufs et al.:"Post–transcriptional regulation of endothelial nitric oxide synthase mRNA stability by Rho GTPhase." Journal of Biological Chemistry, (Sep. 11, 1998) 273 (37) 24266–71.
Ohara et al.:"Regulation of endothelial constitutive nitric oxide synthase by protein C" Hypertension, vol. 25, No. 3, Mar. 1995 pp. 515–420.
Stroes et al.:"Cyclosporin A increases nitric oxide activity in vivo" Hypertension, vol.29, No. 2, Feb. 1997, pp. 570–575.
Lopez–Ongil et al.:"Regulation of endothelial NO synthase expression by cyclosporin A in bovine aortic endothelial cells" American Journal of Physiology, vol. 271, No. 3, Sep. 1996, p. H1072–8.
Patel, J. M. et al. Nitric Oxide Exposure and Sulfhydryl Modulation Alter L–Arginine Transport in Cultured Pulmonary Artery Endothelial Cells. (Abstract Only) Free Radical Radical Biology & Medicine. vol. 20, No. 5. pp. 629. 1996.
Xia, Y. et al. Nitric Oxide Synthase Generates Superoxide and Nitric Oxide in Arginine–Depleted Cells Leading to Peroxynitrite–Mediated Cellular Injury. Proc. Natl. Acad. Sci. USA. vol. 93. pp. 6770–6774. Jun. 1996.
Jeremy, R. W. et al. Effects of Dietary L–Arginine on Atherosclereosis and Endothelium–Dependent Vasolidation in the Hypercholesteralemic Rabbit. Circulation. vol. 94, No. 3. pp. 498–506, Aug. 1, 1996.
Block, E. R. et al. Hypoxia Inhibits L–Arginine Uptake By Pulmonary Artery Endothelial Cells. (Abstract Only) Am. J. Physiol. vol. 269, L574–L580. 1995.
Mayer, B. et al. Brain Nitric Oxide Synthase is a Biopterin–and Flavin–Containing Multi–Functional Oxido–Reductase. (Abstract Only) FEBS 10045. vol. 288, No. 1,2. pp. 187–191. Aug. 1991.

(List continued on next page.)

Primary Examiner—Phyllis G. Spivack
(74) Attorney, Agent, or Firm—Benesch, Friedlander, Coplan & Aronoff, LLP

(57) ABSTRACT

A method for treating a subject who would benefit from increased nitric oxide production comprising administering inhibitors of Hmg-CoA-Reductase is disclosed for the treatment of diseases related to endothelial dysfunction.

14 Claims, 2 Drawing Sheets

OTHER PUBLICATIONS

Weidinger, F. F. et al. Persistent Dysfunction of Regenerated Endothelium After Balloon Angioplasty of Rabbit Iliac Artery. Circulation. vol. 81, No. 5. pp. 1667–1679. May 1990.

Chester, A. H. et al. Low Basal and Stimulated Release of Nitric Oxide in Atherosclerotic Epicardial Coronary Arteries. The Lancet. vol. 336, pp. 897–900. Oct. 13, 1990.

Albina, J. E. et al. Arginine Metabolism in Wounds. Am. J. Physiol. vol. 254. pp. E459–E467. 1988.

Cooke, J.P. et al. Antiatherogenic Effects of L–Arginine in the Hypercholesterolemic Rabbit. (Abstract Only) J. Clin. Invest. vol. 90, No. 3. pp. 1168–1172. Sep. 1992.

Nakamura, Y. et al. Pravastatin Reduces Restenosis After Coronary Angioplasty of High Grade Stenotic Lesions: Results of SHIPS (SHIga Pravastatin Study). (Abstract Only). Cardiovasc. Drugs. Ther., vol. 10, No. 4, pp. 475–483. 1996.

Pohl, U. et al. Effects of LDL on Intracellular Free Calcium and Nitric Oxide–Dependent cGMP Formation on Porcine Endothelial Cells. (Abstract only) Atherosclerosis. vol. 117. pp. 169–178. 1995.

Deliconstantinos, G. et al. Modulation of Particulate Nitric Oxide Synthase Activity and Peroxynitrate Synthesis in Cholesterol Enriched Endothelial Cell Membranes. (Abstract Only) Biochem. Pharm. vol. 49, No. 11. pp. 1589–1600. 1995.

Galle, J. et al. Effect of HDL and Atherogenic Lipoproteins on Formation of $O_2$ and Renin Release in Juxtaglomerular Cells. (Abstract Only) Kidney International. vol. 51, pp. 253–260. 1997.

Bult, H. Nitric Oxide and Atherosclerosis: Possible Implications for Therapy. (Abstract only) Molecular Medicine Today. p. 510. Dec. 1996.

Crouse III, J.R. et al. Pravastatin, Lipids, and Atherosclerosis in the Carotide Arteries (PLAC–II). (Abstract only) Am. J. Cardiol. vol. 75. pp. 455–459. 1995.

Aji, W. et al. L–Arginine Prevents Xanthoma Development and Inhibits Atherosclerosis in LDL Receptor Knockout Mice. (Abstract only) Circulation. vol. 95. pp. 430–437. 1997.

Cooke, J. P. et al. Arginine: A new Therapy for Atherosclerosis?. Circulation. vol. 95. pp. 311–312. 1997.

Boger, R. H. et al. The L–Arginine Nitric Oxide Pathway: Role in Atherosclerosis and Therapeutic Implications. (First page only) Atherosclerosis. vol. 127. pp. 1–11. 1996.

Jay, M.T. et al. Modulation of Vascular Tone By Low Density Lipoproteins. Effects on L–Arginine Transport and Nitric Oxide Synthesis. Experimental Physiology. vol. 82. pp. 349–360. 1997.

Muramatsu, J. et al. Hemodynamic Changes Associated with Reduction in Total Cholesterol By Treatement with the HMG–CoA Reductase Inhibitor Pravastatin. Atherosclerosis. vol. 130. pp. 179–182. 1997.

Sacks, F. M. et al. The Effect of Pravastatin on Coronary Events After Myocardial Infarction in Patients with Average Cholesterol Levels. The New England Journal of Medicine. vol. 335, pp. 1001–1009. Oct. 3, 1996.

Bovan, A. J. van. et al. Reduction of Transient Myocardial Ischemia with Pravastatin in Addition to the Conventional Treatment in Patients with Angina Pectoris, Circulation. vol. 94. pp. 1503–1505. 1996.

Lacoste, L. et al. Comparative Effect of Pravastatin and Simvastatin on Platelet–Thrombus Formation in Hypercholesterolemic Coronary Patients. JACC. vol. 27 No. 2 Supp A. p. 413A. 1996.

Pitt, B. et al. Pravastatin Limitation of Atherosclerosis in the Coronary Arteries (PLAC I): Reduction in Atherosclerosis Progression and Clinical Events. J. Am. Coll. Cardiol. vol. 26. pp. 1133–1139. 1995.

Candipan, R.c. et al. Regression or Progression: Dependency on Vascular Nitric Oxide. Arterioscler. Thromb. Vas. Biol. vol. 16. pp. 45–50. 1996.

Byington, R.P. et al. Reduction in Cardiovascular Events During Pravastatin Therapy. Pooled Analysis of Clinical Events of the Pravastatin Atherosclerosis Intervention Program. Circulation. vol. 92. pp. 2419–2425. 1995.

Pritchard, K.A. et al. Native Low–Density Lipoprotein Increases Endothelial Cell Nitric Oxide Synthase Generation of Superoxide Anion. Circ. Res. vol. 77 No. 3. pp. 510–518. 1995.

Boger, R.H. et al. Supplementation of Hypercholesterolemic Rabbits with L–Arginine Reduces the Vascular Release of Superoxide Anions and Restores NO Production. Artherosclerosis. vol. 117 No. 2. pp. 273–284. 1995.

Lacoste, L. et al. Correction of the Increased Thrombogenic Potential with Cholesterol Reduction. Circulation. vol. 92. pp. 3172–3177. 1995.

Shepard, J. Prevention of Coronary Heart Disease with Provastatin in Men with Hypercholestrolemia. The New England Journal of Medicine vol. 333. pp. 1301–1307. Nov. 16, 1995.

Philis–Tsimikas, A. et al. L–Arginine May Inhibit Atherosclerosis Through Inhibition of LDL Oxidation. Circulation. vol. 92 (Supp. I). pp. 1–422. 1995.

Von der Leyen, H.E. et al. Gene Therapy Inhibiting Neointimal Vascular Lesion: In Vivo Transfer of Endothelial Cell Nitric Oxide Synthase Gene. Proc. Natl. Acad. Sci. USA. vol. 92. pp. 1137–1141. 1995.

Egashira, K. et al. Reduction in Serum Cholesterol with Pravastatin Improves Endothelium–Dependent Coronary Vasomotion in Patients with Hypercholesterolemia. Circulation. vol. 89. pp. 2519–2524. 1994.

Tsao, P. et al. Enhanced Endothelial Adhesiveness in Hypercholesterolemia is Attenuated by L–Arginine. Circulation. vol. 89. pp. 2176–2182. 1994.

Cayatte, A.J. et al. Chronic Inhibition of Nitric Oxide Production Accelerates Neointima Formation and Impairs Endothelial Function in Hypercholesterolemic Rabbits. Arterioscler. Thomb. vol. 14. pp. 753–759. 1994.

Wilcox, J.N. et al. Expression of Multiple Nitric Oxide Synthase Isoforms in Human Aortic Fatty Streaks and Advanced Atherosclerotic Plaques. (Abstract only) Circulation. vol. 90 (Supp. I). pp. I–298. 1994.

Chen, L. Y. et al. Oxidated LDL Decreases L–Arginine Uptake and Nitric Oxide Synthase Protein Expression in Human Platelets: Relevance of the Effect of Oxidized LDL on Platelet Function. Circulation. vol. 93. pp. 1740–1746. 1993.

Wada, H. et al. Hypercoagulable State in Patients with Hypercholesterolemia: Effects of Pravastatin. Clin. Therap. vol. 14. pp. 829–834. 1992.

Drexler, H. et al. Correction of Endothelial Dysfunction in Coronary Microcirculation of Hypercholesterolaemia Patients by L–Arginine. The Lancet. vol. 338. pp. 1546–1550. Dec. 21/28, 1991.

Haman, M. et al. Long–Term Oral Administration of L–Arginine Reduces Intimal Thickening and Enhances Neoendothelium–Dependent Acetylcholine–Induced Relaxation After Arterial Injury. Circulation, vol. 90. No. 3, pp. 1357–1362. Sep., 1994.

Harrison, D.G. Endothelial Modulation of Vascular Tone: Relevance to Coronary Angioplasty and Restenosis. J. Am. Coll. Cardiol. vol. 17. pp. 71B–6B. 1991.

Cooke, J.P. et al. Arginine Restores Cholinergic Relaxation of Hypercholesterolemic Rabbit Thoracic Aorta. Circulation. vol. 83. pp. 1057–1062. 1991.

Witzum, J.L. et al. Role of Oxidized Low Density Lipoprotein in Atherogenesis. J. Clin. Invest. vol. 88. pp. 1785–1792. 1991.

Mugge, A.J. et al. Chronic Treatment with Polyethylene–Glycolated Superoxide Dismutase Partially Restores Endothelium–Dependent Vascular Relaxations in Cholesterol–Fed Rabbits. Circ. Res. vol. 69. pp. 1293–1300. 1991.

Forstermann, U. et al. Selective Attenuation of Endothelium–Mediated Vasodilation in Atherosclerotic Human Coronary Arteries. Circ. Res. vol. 62. pp. 185–191. 1988.

Cohen, R.A. et al. Loss of Selective Endothelial Cell Vasoactive Functions in Pig Coronary Arteries During Hypercholesterolemia. Circ. Res. vol. 63. pp. 903–910. 1988.

Schwarzacher, A.P. et al. Locak Intramural Delivery of L–Arginine Enhances Nitric Oxide Generation and Inhibit Lesion Formation After Balloon Angioplasty. Circulation, vol. 95. No. 7. pp. 1863–1869. Apr. 1, 1997.

Verbeuren, T.J. et al. Effect of Hypercholesterolemia on Vascular Reactivity in the Rabbit., I: Endothelium–Dependent and Independent Contractions and Relaxations in Isolated Arteries of Control and Hypercholesterolemic Rabbits. Circ. Res. vol. 58. pp. 552–564. 1986.

Duggan, D.E. et al. The Physiological Disposition of Lovastatin. Drug Metabolism and Disposition, vol.17, No. 2. pp. 166–173. 1989.

Vickers, S. et al. Metabolic Disposition Studies on Simvastatin, a Cholesterol–Lowering Prodrug. Drug Metabolism and Disposition, vol. 18, No. 2. pp. 138–145. 1990.

* cited by examiner

METHOD OF STIMULATING NITRIC OXIDE SYNTHASE

This Appln is a con't of Ser. No. 08/833,842 filed Apr. 10, 1997, U.S. Pat. No. 5,968,983.

BACKGROUND OF THE INVENTION

This invention relates generally to a method of treating cardio-cerebrorenovascular disease as well as avoiding potential cardiocerebrorenovascular disease, and the symptoms thereof, wherein a substrate of Nitric Oxide Synthase ("NOS") and an agonist of NOS are combined to produce a beneficial effect.

DESCRIPTION OF RELATED ART

Much focus in the area of cardiac disease has been on the presence of cholesterol in the body. Hypercholesterolemia is known to be a primary risk factor for death from coronary heart disease. It is known that 50% or more of the total body cholesterol in humans is derived from intrinsic biosynthesis. It is also known that a rate-limiting step of major significance in the biosynthesis of cholesterol is at the level of the enzyme known as 3-hydroxy-3-methylglutaryl-coenzyme A reductase or Hmg-CoA reductase. A general class of compounds is known in the art which inhibit and reduce the intrinsic biosynthesis of cholesterol in order to reduce the risk factor of hypercholesterolemia and coronary artery death. This general class of compounds is known as inhibitors of Hmg-CoA reductase.

An alternative approach to treating cardiac disease is to effect the dilation of vascular conduits in the body. In this regard, nitric oxide has been shown to be formed enzymatically as a normal metabolite from arginine in vascular endothelium and provides an important component to the formation of endothelium-derived relaxing factor (EDRF). EDRF appears to be equivalent to Endothelium Derived Nitric Oxide (EDNO) and as used herein EDRF and EDNO are interchangeable unless otherwise indicated. Macrophages and neurons have also been shown to produce nitric oxide in the body as a component of their cell killing and/or cytosolic function.

Recently it has been established that a family of enzymes called Nitric Oxide Synthase ("NOS") form nitric oxide from L-arginine, and the nitric oxide produced is responsible for the endothelium dependent relaxation and activation of soluble guanylate cyclase, nuerotransmission in the central and peripheral nervous systems, and activated macrophage cytotoxicity.

Nitric Oxide Synthase, occurs in many distinct isoforms which include a constitutive form (cNOS) and an inducible form (iNOS). The constitutive form is present in normal endothelial cells, neurons and some other tissues. Formation of nitric oxide by the constitutive form in endothelial cells is thought to play an important role in normal blood pressure regulation, prevention of endothelial dysfunction such as hyperlipodemia, arteriosclerosis, thrombosis, and restenosis. The inducible form of nitric oxide synthase has been found to be present in activated macrophages and is induced in vascular smooth muscle cells, for example, by various cytokines and/or microbial products.

The conversion of precursor substrates of EDNO such as L-arginine into nitric oxide is enzymatically catalyzed by NOS and the resulting by-product of the conversion of L-arginine is L-citrulline. Although it was initially described in endothelium, NOS activity has now been described in many cell types. Brain, endothelium, and macrophage isoforms appear to be products of a variety of genes that have approximately 50% amino acid identity. NOS in brain and in endothelium have very similar properties, the major differences being that brain NOS is cytosolic and the endothelial enzyme is mainly a membrane-associated protein.

Functionally, the constitutive form of Nitric Oxide Synthase ("cNOS"), which is the predominant synthase present in brain and endothelium, may be active under basal conditions and can be further stimulated by increases in intracellular calcium that occur in response to receptor-mediated agonists or calcium ionophores. cNOS appears to be the "physiological" form of the enzyme and plays a role in a diverse group of biologic processes. In vitro studies suggest that the activity of nitric oxide synthase can be regulated in a negative feedback manner by nitric oxide itself. In cardiocerebrorenovascular circulation, the primary target for constitutively produced nitric oxide is believed to be soluble guanylate cyclase located in vascular smooth muscle, the myocardium (myocytes) and coronary vascular smooth muscle.

In contrast to the cNOS, the inducible, calcium-independent form, iNOS was initially only described in macrophages. It is now known that induction of nitric oxide synthase can occur in response to appropriate stimuli in many other cell types. This includes both cells that normally do not express a constitutive form of nitric oxide synthase, such as vascular smooth muscle cells, as well as cells such as those of the myocardium that express considerable levels of the constitutive isoform.

iNOS exhibits negligible activity under basal conditions, but in response to factors such as lipopolysaccharide and certain cytokines, expression occurs over a period of hours. The induced form of the enzyme produces much greater amounts of NO than the constitutive form, and induced NOS appears to be the "pathophysiological" form of the enzyme because high concentrations of NO produced by iNOS can be toxic to cells. Induction of iNOS can be inhibited-by glucocorticoids and some cytokines. Relatively little is known about postranscriptional regulation of iNOS. Cytotoxic effects of NO are probably largely independent of guanylate cyclase and cyclic GMP formation. Most of the research in the area has focused on inhibitors of iNOS stimulation using various derivatives of L-arginine.

Research into the area of cNOS activation reveals a number of agonist of cNOS some of which have been described in U.S. Pat. No. 5,543,430, which is hereby incorporated by reference in its entirety. However, until now there was no known research indicating Hmg-CoA reductase inhibitors were capable of functioning as agonist of cNOS.

SUMMARY OF THE INVENTION

The term "subject" as used herein to mean any mammal, including humans, where nitric oxide formation from arginine occurs. The methods herein for use on subjects contemplate prophylactic use as well as curative use in therapy of an existing condition.

The term "native NO" as used herein refers to nitric oxide that is produced through the bio-transformation of L-arginine or the L-arginine dependent pathway. "EDRF" or "EDNO" may be used interchangeably with "native NO". The term endpoints as used herein refers to clinical events encountered in the course of treating cardiovascular disease, up to and including death (mortality).

L-arginine as used herein includes all biochemical equivalents (i.e. salts, precursors, and its basic form). L-arginine as defined herein appears to function as a substrate of cNOS.

"To mix", "mixing", or "mixture(s)" as used herein means mixing a substrate (i.e. L-arginine) and an agonist (i.e. Hmg-CoA reductase inhibitor): 1) prior to administration ("in vitro mixing"); 2) mixing by simultaneous and/or consecutive, but separate (i.e. separate intravenous lines) administration of substrate (L-arginine and agonist to cause "in vivo mixing"; and 3) the administration of a NOS agonist after saturation with a NOS substrate (i.e. L-arginine is administered to build up a supply in the body prior to administering the NOS agonist (nitroglycerin or Hmg-CoA reductase)); or any combination of the above which results in the combination of therapeutic amounts of a NOS agonist and a (NOS substrate in an additive or synergistic way with regard to the treatment of vascular disease.

Agonist refers to an agent which stimulates the bio-transformation of a substrate such as L-arginine to EDNO or EDRF either through enzymatic activation or increasing gene expression (i.e. increased protein levels of c-NOS). Of course, either or both of these mechanisms may be acting simultaneously.

It is an object of this invention to provide a method of preventing, treating, arresting, or ameliorating disease conditions which are benefited by the bio-transformation of a substrate into endogenous nitric oxide or "native" nitric oxide.

It is another object of this invention to provide a method of preventing, treating, arresting, or ameliorating disease conditions which are benefited by the bio-transformation of L-arginine into "native" nitric oxide through enzyme activation of NOS.

It is another object of this invention to ameliorate or avoid tachycardia and prevent or treat ischemia.

It is another object of this invention to achieve a beneficial effect when treating disease conditions by increasing or maximizing the production of "native" nitric oxide, and reducing clinical endpoints to include mortality.

It is another object of this invention to prevent reperfusion injury in subjects who have had abrupt restoration of blood flow.

It is a further object of this invention to provide a mixture of inhibitors of Hmg-CoA reductase and biological equivalents of L-arginine for the treatment of hypertension, hypertensive heart disease, coronary heart disease, including arteriosclerosis, angina, myocardial infarction, coronary thrombosis, restenosis post angioplasty, and sudden death, as well as a wide range of cardiovascular disease (heart failure, stroke, and peripheral vascular diseases), and renovascular ischemia/hypertension.

These and other objects of this invention are provided by one or more of the embodiments provided below.

In one embodiment of the invention, therapeutically effective amounts of a precursor of EDNO and an agonist of NOS are combined prior to administration to a patient. In another embodiment of the invention, therapeutically effective amounts of a precursor of EDNO and an agonist of NOS are combined prior to administered separately and mixed "in vivo".

In another embodiment of the invention, therapeutically effective amounts of L-arginine and inhibitors of Hmg-CoA reductase are mixed at a physiologically acceptable pH and administered to a patient.

In another embodiment of the invention a method for treating hypertension in a subject by vasodilation or vasorelaxation comprises: selecting a hypertensive subject; administering L-arginine and Hmg-CoA reductase inhibitors to the subject; obtaining periodic blood pressure measurements of the subject; and continuing administration of L-arginine and Hmg-CoA reductase inhibitors until a desirable blood pressure or therapeutic effect is detected in the subject. A desirable blood pressure in a hypertensive subject should ultimately be within the following ranges: systolic preferably in the range of 95–180 mmHg, more preferably in the range of 105–165 mmHg, and even more preferably in the range of 120 to 140 mmHg; and diastolic preferably in the range of 55–115 mmHg, more preferably in the range of 65–100 mmHg, and even more preferably in the range of 70 to 90 mmHg, and most preferably 75–85 mmHg. Under no circumstances should the systolic be permitted to go below 95 mmHg.

Another embodiment of the present invention is a method for preventing or treating cardiovascular disease in a non-hypertensive subject by vasodilation or vasorelaxation comprising: selecting a subject; administering to said subject a formulation comprising a mixture of an inhibitor of Hmg-CoA reductase and an endothelium dependent source of nitric oxide (i.e., L-arginine); obtaining periodic measurements of vasorelaxation on the subject and; continuing administration of the formulation until a desirable state of vasorelaxation or desirable therapeutic effect is detected on the subject. A desirable state-of vasorelaxation is for example a lowering of the systolic by about 20 mmHg and a lowering of the diastolic by about 10 mmHg. Under no circumstances should the systolic be lowered less than 95 mmHg.

Yet another embodiment is a method for stimulating cNOS in a subject which comprises: selecting a subject; administering to said subject a formulation comprising a mixture of L-arginine and inhibitors of Hmg-CoA reductase, so as to maximize "native" NO production and reduce endpoints to include mortality.

DETAILED DESCRIPTION OF THE PREFERRED EMBODIMENTS

Figure 1:
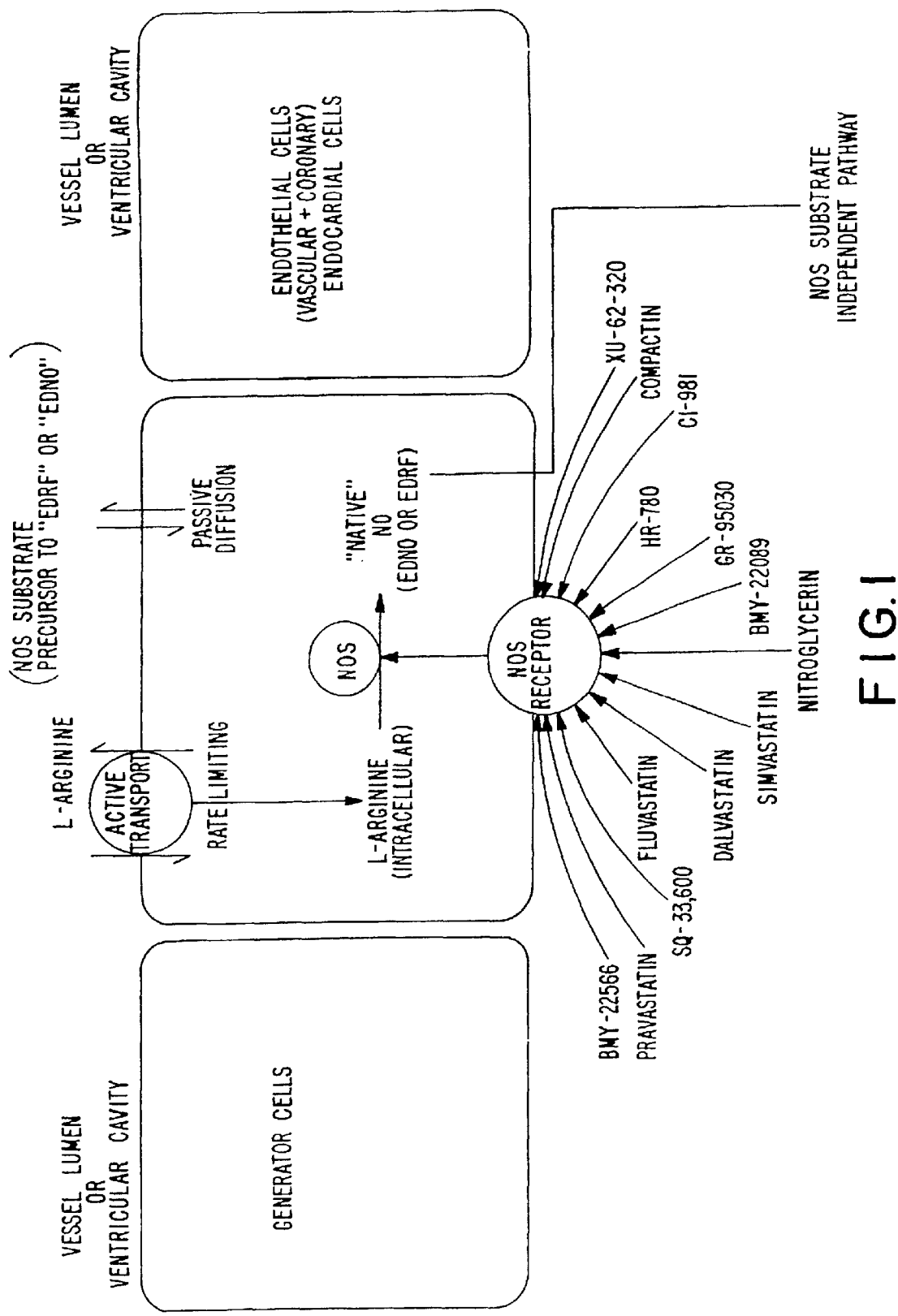
FIG. 1 is a schematic representation of the proposed NOS activation pathway.

From the data presented herein it appears that inhibitors of Hmg-CoA reductase may have dual applicability in the treatment of hypertension and cardiovascular diseases such that they act as both an inhibitor of the intrinsic biosynthesis of cholesterol and a stimulator or agonist of nitric oxide synthase. The fact that Hmg-CoA reductase may be agonist or stimulant of nitric oxide synthase has remarkable implications. Mixing inhibitors of Hmg-CoA reductase "in vitro" or "in vivo" with L-arginine has been found to have an unforeseen beneficial effect that is most likely due to excess L-arginine providing additional substrate for the nitric oxide synthase and the NOS being catalyzed to enzymatically increase the bio-transformation of L-arginine into nitric oxide.

Stimulation of NOS in the presence of excess L-arginine or other substrate precursor of native NO (EDRF or EDNO) may be used to prevent, treat, arrest, or ameliorate any disease or condition which is positively affected by NO production. Such conditions include hypertensive cardiocerebrorenovascular diseases and their symptoms as well as non-hypertensive cardiocerebrorenovascular diseases. The mixture is particularly useful for subjects in need of native NO production. Application of such a mixture is beneficial for: (1) Chronic stable angina; (2) Unstable angina; (3) Acute myocardial infarction; (4) Hibernating myocardium; (5) Stunned myocardium; (6) Limitation of ventricular remodeling in post myocardial infarction and subsequent risk of congestive heart failure; (7) Prophylaxis of recurrent myocardial infarction; (8) Prevention of sudden death following myocardial infarction; (9) Vasospastic angina; (10) Congestive heart failure-systolic-seen in association with 1–6 above; (11) Congestive heart failure-diastolic-seen in association with 1–10 above and 12–15 below; (12) Microvascular angina seen in association with 1–11 above and 15 and 16 below; (13) Silent ischemia seen in association with 1–12 above and 15 and 16 below; (14) Reduction of ventricular ectopic activity seen in association with 1–13 above and 15 below; (15) Any or all of the above 1–14 states of ischemic myocardium associated with hypertensive heart disease and impaired coronary vasodilator reserve; (16) control of blood pressure in the treatment of hypertensive crisis, perioperative hypertension, uncomplicated essential hypertension and secondary hypertension; (17) Regression of left ventricular hypertrophy seen in association with 15 and 16 above; (18) Prevention and or regression of epicardial coronary arteriosclerosis seen in 1–17 above; (19) Prevention of restenosis post angioplasty; (20) Prevention and/or amelioration of free radical mediated reperfusion injury in association with 1–19 above; (21) Use of the combination in the prevention of myocardial injury during cardioplegic arrest during coronary bypass or other open heart surgery i.e. use of the combination as a cardioplegic solution; (22) Post transplant cardiomyopathy; (23) Renovascular ischemia; (24) Cerebrovascular ischemia (TIA) and stroke); and (25) Pulmonary hypertension.

Vascular smooth muscle cells are located mainly in veins, arteries, and coronary arteries. The following discussion focuses on smooth muscle and myocyte relaxation stimulated by vasodilators. As discussed above the nitric oxide synthase in the cells is normally cNOS, the constitutive form of nitric oxide synthase, and the generator cells are endothelial cells and the target cells are vascular smooth muscle cells. FIG. 1 is a schematic illustration and is not intended to imply any cellular relationship or geography of the various sites of action, but rather meant to illustrate their functional relationship.

The principle combination to be employed will be a mixture that involves therapeutic concentrations of L-arginine and a Hmg-CoA reductase inhibitor in water. Any pharmaceutical grade L-arginine will be sufficient and should be diluted preferably to 2.5–60% w/v (g/ml), more preferably to 5–45% w/v (g/ml), even more preferably between 7.5–30% w/v (g/ml), even more preferably to 10–15% w/v (g/ml), and most preferably 10% w/v (g/ml) L-arginine. The typical doses anticipated will be 30 grams of L-arginine in sterile water (Total Volume 300 cc). L-arginine is anticipated eventually to be approximately 10:1 to about 25:1 of the hydrochloride salt to L-arginine as a base, and even more preferably 15:1 to about 20:1 hydrochloride salt to base, and most preferably 15:1 hydrochloride salt to base. In this example 28 to 29 grams will be the hydrochloride salt and 1 to 2 grams of L-arginine will be base.

L-arginine may be used in conjunction with virtually any of the family of those substances known as Hmg-CoA reductase inhibitors. Those particular Hmg-CoA reductase inhibitors most preferred for use in conjunction with the present formulation as selected from the group consisting of: simvastatin, lovastatin, pravastatin, compactin, fluvastatin, dalvastatin, HR-780, GR-95030, CI-981, BMY 22089, and BMY 22566. U.S. Pat. No. 5,316,765 cites a number of these Hmg-CoA reductase inhibitors and is hereby incorporated by reference in its entirety. In particularly preferred embodiments of the present invention, the Hmg-CoA reductase inhibitor utilized is pravastatin or lovastatin. In an even more particularly preferred embodiments, the administration of the present invention includes the Hmg-CoA reductase inhibitor pravastatin.

As part of a "mixture", the Hmg-CoA reductase inhibitor is included together with L-arginine and clinically effective weight ratios of between 1:2 to 1:150. Even more particularly, the ratio of the Hmg-CoA reductase Larginine in the formulation is between 1:5 to 1:100. The most preferred embodiment of the "mixture" the ratio of Hmg-CoA reductase inhibitor, most particularly pravastatin, to L-arginine is 1:50. The range of ratios of an Hmg-CoA reductase inhibitor to L-arginine may be employed with virtually any Hmg-CoA reductase inhibitor.

Where the particular Hmg-CoA reductase inhibitor is pravastatin, the ratio of pravastatin to L-arginine is preferably within the range 1:2 to 1:50, Wt/Wt. For example, pravastatin/L-arginine at a ratio of 1:2 would include 40 mg/day pravastatin with 80 mg/day L-arginine. Where the ratio of pravastatin/L-arginine is at a ratio of 1:20, for example, 20 mg/day pravastatin would be administered with 400 mg/day L-arginine. Weight ratio of ingredients described herein in regard to the Hmg-CoA reductase inhibitors, lovastatin and pravastatin are applicable for any Hmg-CoA reductase inhibitor. The amounts above have been found to be effective, however, each route of administration (i.e. IV, oral, transdermal, etc.) will vary in their requirements.

Even more particularly, the presently disclosed "mixtures" may be described in terms of their relative concentrations (grams) administered as part of a continuous daily and/or monthly regimen. In one particular embodiment, the formulation is administered so as to provide the patient with between 20–40 milligrams per day of the Hmg-CoA reductase inhibitor (i.e., pravastatin) together with a daily dose of L-arginine of between 100 to 200 mg per day. Most preferably, the Hmg-CoA reductase inhibitor, such as lovastatin, is administered at a daily dose of about 20 mg per day together with a dose of about 200 mg per day L-arginine. This particular embodiment of the claimed formulation should maintain within the patient efficient levels of the formulation.

By way of example only, Table 1 presents a listing of several inhibitors of Hmg-CoA reductase. These substances vary in their potency and their abilities to inhibit Hmg-CoA.

TABLE 1

Simvastatin
Lovastatin
Pravastatin
Compactin (a.k.a., mevastatin)
Fluvastatin
Dalvastatin
GR-95030
HR-780
SQ 33,600
BMY 22089
BMY 22566
CI 981

The Hmg-CoA reductase inhibitors of the present invention are also characterized by an ability to stimulate receptor-mediated clearance of hepatic low-density lipoproteins (LDL), as an anti-hypercholesterolemic, and as a competitive inhibitor of Hmg-CoA reductase.

The Hmg-CoA reductase inhibitor employed may be lovastatin, simvastatin, pravastatin, XU-62-320 (Sodium 3.5-dihydroxy-7 [3-(4-fluorophenyl)-1(methylethyl)-IH-Indole-2yl]-hept-6-enoate), mevastatin (a.k.a., compactin), BNY 22089, CI-981, SQ 33,600, BMY 22089, CI 981, HR 780, SQ 33,600 or any other member of the class of compounds that inhibit Hmg-CoA reductase. The preparation of lovastatin, simvastatin, and pravastatin have been described in the patent literature. The preparation of XU-62-320 (fluvastatin) is described in WIPO Patent W084/02131. BMY 22089(13), CI 981(14), HR 780(15), and SQ 33,600 (16) are also described in the literature cited, and are specifically incorporated herein by reference for the purpose of even more fully describing the chemical structure and synthesis of these Hmg-CoA reductase inhibitors. These methods of preparation are hereby incorporated by reference in their entirety.

Also within the scope of those Hmg-CoA reductase inhibitors of the present invention are included the bio-active metabolites of those compounds listed in Table 1, such as pravastatin sodium (the bio-active metabolite of mevastatin).

Any one or several of those Hmg-CoA reductase inhibitor compounds listed in Table 1 pravastatin may be mixed with L-arginine or substrate precursor to endogenous nitric oxide to provide a therapeutically effective treatment for a patient.

Until now there was no link between the bio-transformation of L-arginine into "native" nitric oxide and anti-hypocholesterolemic Hmg-CoA reductase inhibitors. However, it is now believed that Hmg-CoA reductase inhibitors has a stimulating effect on cNOS. The mechanism is not well understood but it appears the mixture of inhibitors of Hmg-CoA reductase and L-arginine may have a heretofore unexpected synergistic effect on cNOS stimulation. The stimulation of cNOS may be a result of cNOS having a unique receptor site for Hmg reductase inhibitors or inhibitors of Hmg-CoA reductase initiating a cascade of events which stimulate NO. Administering the two also provides adequate substrate for cNOS processing of L-arginine since the L-arginine is added in excess while at the same time stimulation the enzymatic activity of NOS. Whether it is a synergistic effect or additive effect, what is clear is that "mixing" a precursor substrate of "native" nitric oxide with a Hmg-CoA reductase inhibitor results in a heretofore unexpected increase in NO production. This unexpected affect is demonstrated in the example below.

EXAMPLE

The direct effects of acteylcholine and pravastatin on NO production in bovine aortic endothelial cells (BAEC) was determined using a highly sensitive photometric assay for conversion of oxyhemoglobin to methemoglobin. NO oxidize; oxyhemoglobin ($HbO_2$) to methemoglobin (metHb) in the following reaction $HbO_2+NO \rightarrow metHb+NO_3$. The amount of NO produced by endothelial cells was quantified by measuring the change in absorbance as $HbO_2$ oxidizes to metHb. Oxyhemoglobin has a absorbance peak at 415 nm, while metHb has a 406 nm absorbance peak. By subtracting the absorbance of metHb from $HbO_2$, the concentration of NO can be assessed. The general method was patterned after that of Feelisch et al., (Biochem. and Biophy. Res. Comm. 1991; 180, Nc I:286–293).

For this assay, endothelial cells were isolated from bovine aortas. BAECs were grown to confluency in 150 mm plates (Corning) using Medium 199 supplemented with penicillin G (100 mL$^{-1}$), streptomycin (100 mg mL$^{-1}$), glutamine (100 mg mL$^{-1}$), thymidine (100 mg mL$^{-1}$), and 10% fetal calf serum (Gibco). Upon confluency, cells will be washed twice with a 1% phosphate buffered saline/EDTA solution. Tripsin/EDTA was added and the cells were kept at 37° C. until the cells become rounded thus signaling detachment from the plate. An equal amount of trypsin inhibitor was added to inhibit any further trypsin activity that might damage the cells. The cells were pelleted by spinning at 150–200 g for 5 min. Cells were resuspended in culture medium and approximately $10^7$ of these cells were used to inoculate 0.5 g of micro-carrier beads (Cytodex #3). Cells, beads and medium was transferred to a spinner flask (Wheaton) where the culture sat undisturbed at 37° C. with 95% $O_2$ and 5% $CO_2$ for 29 min then spun (20 rpm) in this same environment for 1 min. This sitting cycle allowed for cell adherence to the beads while the spinning created an even distribution of cells and beads. After 4 hrs of this attachment phase, the spinner flask was left on the stirrer at slow speed for 2–3 days for uniform cellular coating of beads.

Beads/cells were rinsed twice and then suspended in a Hepes-buffered Krebs-Ringer solution containing all necessary co-factors. To prevent a reaction between NO and superoxide ($O_2$), superoxide dismutase (200 U/ml) was added to the buffer. Catalase (100 U/ml) will be added to decompose hydrogen peroxidase, keeping the hemoglobin active. Two ml of EC/beads were placed into a water-jacketed chromatography column (Pharmacia) and superfused at 2 ml/min with Hepes-buffered Krebs-Ringers solution containing 3 uM oxyhemoglobin. The perfusate was then directed into a flow-through cuvettte in a dual wavelength spectrophotometer and absorbance was measured to determine the basal and stimulated NO release. A parallel column circuit was filled with only beads (no cells) to determine basal and spontaneous release of NO in this system without cells. Vehicle (buffer w/o agent) did not cause a change in absorbance when infused into the cell-bead column.

Experimental stimulation were carried out by 3 min infusion periods of acetylcholine (ACH) or pravastatin (PRA) added to buffer perfusion using a micro syringe pump at a rate of 45 ul/min to yield a final concentration of $10^{-6}$ and $10^{-5}$M for ACH and $10^{-6}$ and $10^{-5}$M for PRA in the buffer. The effects of buffer containing L-Name ($10^{-3}$M) in blocking the actions of these drug agents and then a buffer without L-NAME but with excess L-arginine ($10^{-3}$M) in reversing any L-NAME effect was examined. Each drug agent concentration was given twice for each of the three buffer systems; a period of 10 min was allowed between infusion of agents. Our data demonstrate that this cell perfusion and monitoring system remains stable for at least 4–6 hours. At the end of each experiment, cell viability was checked using trypan blue exclusion.

For analysis, we determined the area under the curve for the change in absorbance response/unit time (min) caused by each agent above baseline levels and calculated metHb production using an extinction coefficient of 39 mM$^1$. During the 3 min infusion of agents, absorbance increases rapidly. Changes in absorbance to these agents usually persist from 2–8 mins depending on the size of the response before returning to baseline levels. We assume a one to one correspondence for NO and metHb production, the known stoichiometric balance for this reaction. We also determined changes in basal NO production during perfusion with each of the buffer systems. Basal NO values were subtracted from any drug-induced responses to determine NO production which results from the drug's actions. Table 2 recites the results of these experiments.

TABLE 2

|  | Basic Buffer | $10^{-3}$M L-NAME | $10^{-3}$M L-arginine |
|---|---|---|---|
|  | (absolute production of NO in nmole* min) | | |
| $10^{-6}$M Ach | 197.60 | 72.20 | 330.60 |
| $10^{-5}$M Ach | 619.40 | 288.80 | 756.20 |
| $10^{-6}$M Prav. | 163.40 | 45.60 | 201.40 |
| $10^{-5}$M Prav. | 513.00 | 209.00 | 752.40 |

Figure 2:
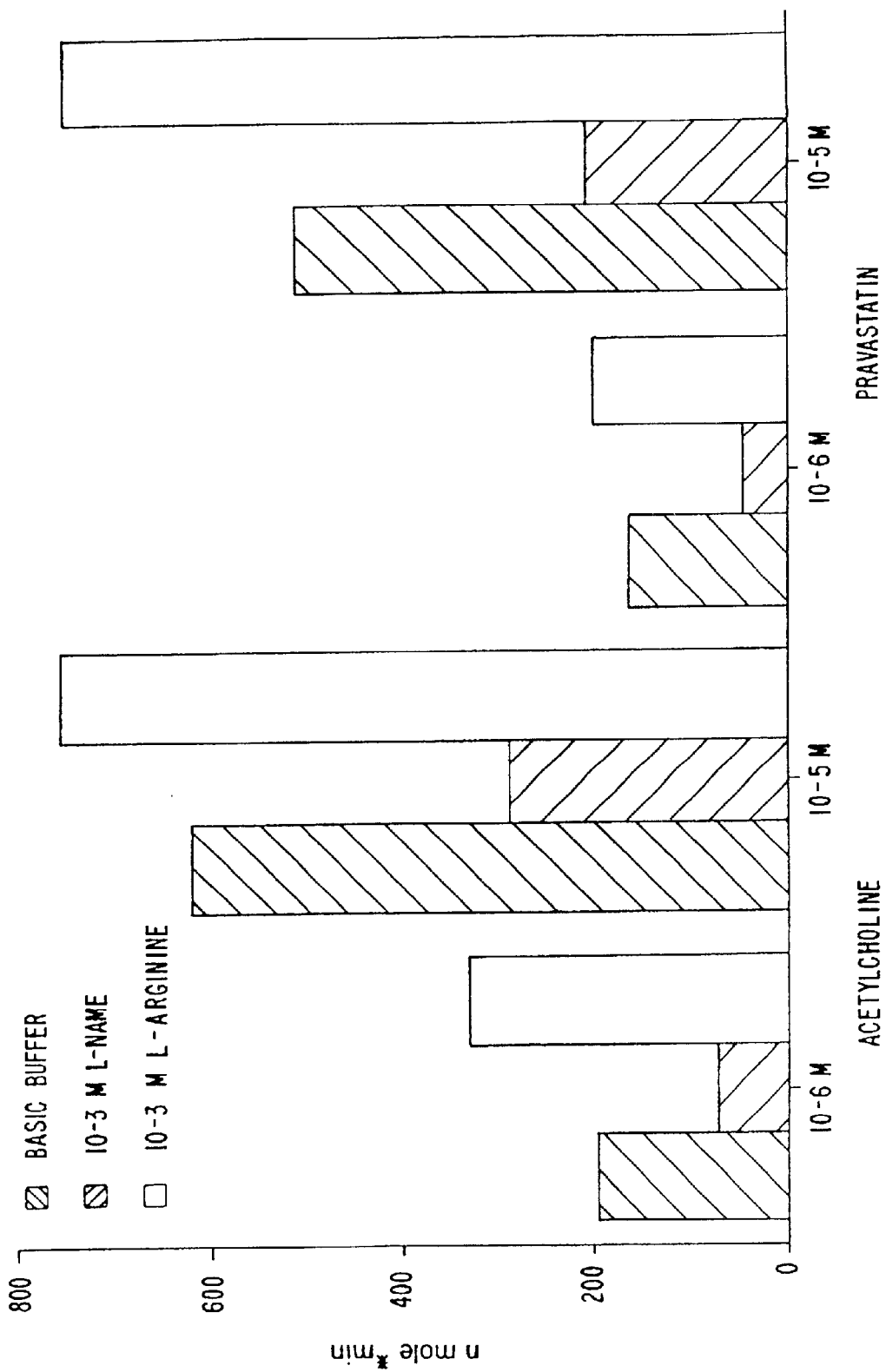
FIG. 2 is a bar graph illustrating the stimulation of NOS with pravastatin.

FIG. 2 is a bar graph of the data generated which illustrates the effects of acetylcholine and pravastatin ($10^{-6}$ and $10^{-5}$ M) administered for 3 min periods into the cell/bead perfusion system on NO production with: 1) $10^{-5}$ M L-arginine in control (basic) buffer, 2) $10^{-3}$ M of L-NAME in buffer, and 3) $10^{-3}$ M of L-arginine in buffer. Responses are transient elevations in NO production above basal levels. Data for responses in L-NAME and L-arginine augmented buffer are presented as percent of response in control buffer (100%); numbers in basic buffer bars indicate absolute production of NO in nmole *min. The remaining two bars denote differences between responses in L-NAME buffer vs both basic and L-arginine added buffers.

The effects of pravastatin on activity of endothelial cells in producing NO were compared with those of actetylcholine, which is known to specifically stimulate NO production by NOS activity. Adding acetylcholine to the buffer superfusion bovine aortic endothelial cells (BAECs) grown on beads increased their production of NO as measured by oxidation of oxyhemoglobin to methemoglobin (FIG. 2) Acetylcholine produced a transient, concentration-related increase in NO above baseline levels. In basic buffer containing $5\times10^{-5}$M L-arginine, and there was approximately a two fold increase in NO production between $10^{-5}$ M L-arginine, there was approximately a two fold increase in NO production between $10^{-5}$ and $10^{-6}$ M acetylcholine. Subsequent treatment of these cells with buffer containing L-NAME, $10^{-3}$ M markedly reduced acetylcholine-induced production of NO by 80%. When this L-NAME buffer was replaced with another containing increased L-arginine ($10^{-3}$ M), acetylcholine-elicited production of NO returned to control levels.

Pravastatin also caused a concentration-related increase in NO production above baseline levels. There was a larger increment in response to the $10^{-5}$ M concentrations of pravastatin (~3 X) compared with that of acetylcholine. Superfusion of the cell suspension with L-NAME ($10^{-3}$ M), also blunted NO production in response to pravastatin. This suggests that NO production is due at least in part to NOS activity. Subsequent perfusion of the cells with a buffer containing L-arginine $10^{-3}$ M resulted in a return in NO production to a level above the amount induced by the Pravastatin in control (basis) buffer. This restoration of response to Pravastatin after L-arginine addition was greater than that observed for acetylcholine. Administration of Pravastatin or acetylcholine into a perfusion system containing only beads without cells did not induce metHb/NO production.

As can be seen from Table 2 and FIG. 2, pravastatin appears to stimulate cNOS in much the same way as other NOS agonist described in U.S. Pat. No. 5,543,430 independent of its inhibitory effect on cholesterol biosynthesis.

Although the preferred methods have been described in detail, it should be understood that various changes, substitutions, and alterations can be made in the present invention as defined by the claims appended hereto. For example, other cNOS agonist may be identified. An example of a contemplated formulation is a mixture of estrogen and L-arginine since preliminary data indicates that estrogen may be functioning as a NOS agonist. The present invention is defined by the claims attached hereto.

What is claimed is:

1. A method for treating a subject who would benefit from increased Nitric Oxide production in a tissue comprising:
   administering to the subject in need of such treatment, irrespective of the subject's cholesterol level, a Hmg-CoA reductase inhibitor in an amount effective to increase Nitric Oxide production in said tissue of the subject.

2. The method of claim 1 wherein the subject is nonhyperlipidemic.

3. The method of claim 2 wherein said amount is sufficient to increase Nitric Oxide production above normal baseline levels.

4. The method of claim 2 wherein the subject has a cytokine-induced condition comprising an abnormally low level of nitric oxide synthase activity.

5. The method of claim 2, wherein the subject has an abnormally elevated risk of pulmonary hypertension.

6. The method of claim 2, wherein the subject has pulmonary hypertension.

7. The method of claim 1 wherein the subject has a condition comprising an abnormally low level of endothelial cell Nitric Oxide Synthase activity.

8. The method of claim 1 wherein the Hmg-CoA reductase inhibitor is selected from the group consisting of simvastatin, lovastatin, pravastatin, compactin, fluvastatin, and dalvastatin.

9. The method of claim 1 wherein the Hmg-CoA reductase inhibitor is simvastatin.

10. The method of claim 1 wherein the Hmg-CoA reductase inhibitor is lovastatin.

11. The method of claim 1 wherein the Hmg-CoA reductase inhibitor is pravastatin.

12. The method of claim 1 wherein the Hmg-CoA reductase inhibitor is fluvastatin.

13. The method of claim 1 wherein the Hmg-CoA reductase inhibitor is dalvastatin.

14. The method of claim 1 wherein the Hmg-CoA reductase inhibitor is compactin.

* * * * *

US006465516C1

(12) EX PARTE REEXAMINATION CERTIFICATE (8138th)
United States Patent
Kaesemeyer

(10) Number: US 6,465,516 C1
(45) Certificate Issued: Apr. 5, 2011

(54) METHOD OF STIMULATING NITRIC OXIDE SYNTHASE

(75) Inventor: Wayne H. Kaesemeyer, Augusta, GA (US)

(73) Assignee: Palmetto Pharmaceuticals, LLC, Saint Simons Island, GA (US)

Reexamination Request:
No. 90/009,684, Mar. 26, 2010

Reexamination Certificate for:
Patent No.: 6,465,516
Issued: Oct. 15, 2002
Appl. No.: 09/420,328
Filed: Oct. 18, 1999

Related U.S. Application Data

(63) Continuation of application No. 08/833,842, filed on Apr. 10, 1997, now Pat. No. 5,968,983.

(51) Int. Cl.
*A61K 31/21* (2006.01)
*A61K 31/22* (2006.01)
*A61K 31/40* (2006.01)
*A61K 31/41* (2006.01)
*A61K 31/44* (2006.01)
*A61K 31/185* (2006.01)
*A61K 31/198* (2006.01)
*A61K 31/351* (2006.01)
*A61K 31/365* (2006.01)
*A61K 31/662* (2006.01)
*A61K 31/675* (2006.01)
*A61K 45/00* (2006.01)
*A61K 38/18* (2006.01)
*A61P 9/00* (2006.01)
*A61P 43/00* (2006.01)

(52) U.S. Cl. .................. 514/548; 514/419; 514/460
(58) Field of Classification Search .............. 514/548
See application file for complete search history.

(56) References Cited

U.S. PATENT DOCUMENTS

| | | | |
|---|---|---|---|
| 2,968,158 A | 1/1961 | Ruschig et al. |
| 3,035,975 A | 5/1962 | Voigt |
| 3,097,242 A | 7/1963 | Hoehn et al. |
| 3,291,689 A | 12/1966 | Nordmann |
| 3,454,635 A | 7/1969 | Weber et al. |
| 3,501,495 A | 3/1970 | Beregi et al. |
| 3,625,214 A | 12/1971 | Higuchi |
| 3,654,357 A | 4/1972 | Bretschneider et al. |
| 3,668,215 A | 6/1972 | Plumpe et al. |
| 3,669,966 A | 6/1972 | Ambrogi et al. |
| 3,708,486 A | 1/1973 | Kutter et al. |
| 3,983,140 A | 9/1976 | Endo et al. |
| 4,062,950 A | 12/1977 | Frommer et al. |
| 4,174,439 A | 11/1979 | Rauenbusch et al. |
| 4,231,938 A | 11/1980 | Monaghan et al. |
| 4,254,256 A | 3/1981 | Otani et al. |
| 4,259,314 A | 3/1981 | Lowey |
| 4,287,200 A | 9/1981 | Kawamatsu et al. |
| 4,287,202 A | 9/1981 | Horrobin |
| 4,346,227 A | 8/1982 | Terahara et al. |
| 4,351,844 A | 9/1982 | Patchett et al. |
| 4,369,172 A | 1/1983 | Schor et al. |
| 4,389,393 A | 6/1983 | Schor et al. |
| 4,448,784 A | 5/1984 | Glamkowski et al. |
| 4,450,171 A | 5/1984 | Hoffman et al. |
| 4,499,289 A | 2/1985 | Baran et al. |
| 4,567,264 A | 1/1986 | Kluge et al. |
| 4,572,912 A | 2/1986 | Yoshioka et al. |
| 4,590,062 A | 5/1986 | Jang |
| 4,613,610 A | 9/1986 | Wareing |
| 4,629,620 A | 12/1986 | Lindahl et al. |
| 4,634,765 A | 1/1987 | Junge et al. |
| 4,663,325 A | 5/1987 | Ohtaka et al. |
| 4,686,237 A | 8/1987 | Anderson |
| 4,687,777 A | 8/1987 | Meguro et al. |

(Continued)

FOREIGN PATENT DOCUMENTS

| | | |
|---|---|---|
| DE | 19913528 A1 | 6/2000 |
| EP | 194686 B1 | 12/1989 |
| EP | 0407780 A | 1/1991 |
| EP | 217379 B1 | 7/1991 |
| EP | 441119 A3 | 10/1992 |
| EP | 0350246 B1 | 6/1993 |
| EP | 463061 B1 | 6/1993 |
| EP | 0546796 | 7/1993 |
| EP | 0745332 A1 | 12/1996 |
| EP | 0114027 B1 | 1/1998 |
| EP | 1023060 A1 | 4/1999 |
| EP | 498482 B1 | 9/1999 |
| EP | 708647 B1 | 5/2000 |
| EP | 1175210 A1 | 9/2000 |
| EP | 1175246 A1 | 9/2000 |
| EP | 1212101 A1 | 3/2001 |
| EP | 730448 B1 | 2/2002 |
| EP | 745332 B1 | 9/2004 |
| EP | 784429 B1 | 1/2005 |
| EP | 1003501 B1 | 3/2005 |

(Continued)

OTHER PUBLICATIONS

Amin et al., "RG 12561 (dalvastatin): a novel synthetic inhibitor or HMG–CoA reductase and cholesterol–lowering agent," Abstract, Pharmacology, 46(1): 13–22, 1993.*

Akira, Endo, "The discovery and development of HMG–CoA reductase inhibitors," J. Lipid Research, 33: 1569–1588, 1992.*

Ridker et al., "Rosuvastatin in the Primary Prevention of Cardiovascular Disease Among Patients with Low Levels of Low–Density Lipoprotein Cholesterol and Elevated High–Sensitivity C–Reactive Protein," Circulation 108: 2292–2297, 2003.*

(Continued)

*Primary Examiner*—Gary L. Kunz

(57) ABSTRACT

A method for treating a subject who would benefit from increased nitric oxide production comprising administering inhibitors of Hmg-CoA-Reductase is disclosed for the treatment of diseases related to endothelial dysfunction.

U.S. PATENT DOCUMENTS

| | | |
|---|---|---|
| 4,701,559 A | 10/1987 | Horii et al. |
| 4,739,073 A | 4/1988 | Kathawala |
| 4,789,734 A | 12/1988 | Pierschbacher |
| 4,857,522 A | 8/1989 | DiPietro et al. |
| 4,873,255 A | 10/1989 | Yoshioka et al. |
| 4,882,167 A | 11/1989 | Jang |
| 4,897,405 A | 1/1990 | Alessi et al. |
| 4,902,630 A | 2/1990 | Bennett et al. |
| 4,906,474 A | 3/1990 | Langer et al. |
| 4,912,107 A | 3/1990 | Kleinschroth et al. |
| 4,920,098 A | 4/1990 | Cotter et al. |
| 4,925,673 A | 5/1990 | Steiner et al. |
| 4,937,232 A | 6/1990 | Bell et al. |
| 4,965,200 A | 10/1990 | Chen et al. |
| 4,983,396 A | 1/1991 | Bodor et al. |
| 4,990,519 A | 2/1991 | Jones et al. |
| 5,002,953 A | 3/1991 | Hindley |
| 5,003,065 A | 3/1991 | Merritt et al. |
| 5,030,447 A | 7/1991 | Joshi et al. |
| 5,061,717 A | 10/1991 | Clark et al. |
| 5,084,482 A | 1/1992 | Hirsch et al. |
| 5,091,524 A | 2/1992 | Vertesy et al. |
| 5,106,836 A | 4/1992 | Clemens et al. |
| 5,116,870 A | 5/1992 | Smith et al. |
| 5,120,754 A | 6/1992 | Clark et al. |
| 5,132,317 A | 7/1992 | Cantello et al. |
| 5,132,407 A | 7/1992 | Stuehr et al. |
| 5,135,935 A | 8/1992 | Alberts et al. |
| 5,140,012 A | 8/1992 | McGovern et al. |
| 5,141,957 A | 8/1992 | Jiang et al. |
| 5,147,650 A | 9/1992 | Fregly et al. |
| 5,157,116 A | 10/1992 | Decep et al. |
| 5,171,217 A | 12/1992 | March et al. |
| 5,180,589 A | 1/1993 | Joshi et al. |
| 5,190,970 A | 3/1993 | Pan et al. |
| 5,192,772 A | 3/1993 | Yoshikuni et al. |
| 5,204,370 A | 4/1993 | Jiang et al. |
| 5,216,014 A | 6/1993 | Jiang et al. |
| 5,217,997 A | 6/1993 | Levere et al. |
| 5,223,522 A | 6/1993 | Clark et al. |
| 5,254,331 A | 10/1993 | Mausner |
| 5,260,275 A | 11/1993 | Cooper et al. |
| 5,260,440 A | 11/1993 | Hirai et al. |
| 5,266,594 A | 11/1993 | Dawson et al. |
| 5,270,310 A | 12/1993 | Bell et al. |
| 5,270,323 A | 12/1993 | Milne et al. |
| 5,272,258 A | 12/1993 | Siegel et al. |
| 5,273,875 A | 12/1993 | Griffith |
| 5,273,995 A | 12/1993 | Roth |
| 5,278,189 A | 1/1994 | Rath et al. |
| 5,281,627 A | 1/1994 | Griffith |
| H1286 H | 2/1994 | Eisman et al. |
| 5,286,739 A | 2/1994 | Kilbourn et al. |
| 5,298,497 A | 3/1994 | Tschollar et al. |
| 5,300,288 A | 4/1994 | Albright |
| 5,326,569 A | 7/1994 | Acosta et al. |
| 5,354,772 A | 10/1994 | Kathawala |
| 5,366,738 A | 11/1994 | Rork et al. |
| 5,374,651 A | 12/1994 | Kilbourn et al. |
| 5,385,940 A | 1/1995 | Moskowitz |
| 5,395,612 A | 3/1995 | Griffith et al. |
| 5,405,919 A | 4/1995 | Keefer et al. |
| 5,441,946 A | 8/1995 | Pauls et al. |
| 5,447,922 A | 9/1995 | Lawrence et al. |
| 5,451,409 A | 9/1995 | Rencher et al. |
| 5,461,039 A | 10/1995 | Tschollar et al. |
| 5,461,146 A | 10/1995 | Lewis et al. |
| 5,470,832 A | 11/1995 | Gibbs et al. |
| 5,470,845 A | 11/1995 | Magnin et al. |
| 5,470,847 A | 11/1995 | Garfield et al. |
| 5,475,029 A | 12/1995 | Bradfute et al. |
| 5,481,003 A | 1/1996 | Gillig et al. |
| 5,482,925 A | 1/1996 | Hutsell |
| 5,488,145 A | 1/1996 | Carney |
| 5,488,167 A | 1/1996 | Hudlicky |
| 5,491,242 A | 2/1996 | Gillig et al. |
| 5,500,345 A | 3/1996 | Soe et al. |
| 5,504,078 A | 4/1996 | Ducep et al. |
| 5,506,229 A | 4/1996 | Dow et al. |
| 5,508,045 A | 4/1996 | Harrison et al. |
| 5,514,696 A | 5/1996 | Murugesan et al. |
| 5,519,035 A | 5/1996 | Maiese et al. |
| 5,530,001 A | 6/1996 | Nakajima et al. |
| 5,543,154 A | 8/1996 | Rork et al. |
| 5,543,430 A | 8/1996 | Kaesemeyer |
| 5,545,636 A | 8/1996 | Heath, Jr. et al. |
| 5,558,838 A | 9/1996 | Uffenheiner |
| 5,565,448 A | 10/1996 | Nambi et al. |
| 5,576,351 A | 11/1996 | Yoshimura et al. |
| 5,578,590 A | 11/1996 | Grunicke et al. |
| 5,582,838 A | 12/1996 | Rork et al. |
| 5,583,101 A | 12/1996 | Stamler et al. |
| 5,591,772 A | 1/1997 | Lane et al. |
| 5,593,971 A | 1/1997 | Tschollar et al. |
| 5,602,098 A | 2/1997 | Sebti et al. |
| 5,604,256 A | 2/1997 | Kogen et al. |
| 5,612,359 A | 3/1997 | Murugesan |
| 5,616,577 A | 4/1997 | Nambi et al. |
| 5,620,876 A | 4/1997 | Davis et al. |
| 5,621,098 A | 4/1997 | Heath, Jr. et al. |
| 5,621,101 A | 4/1997 | Lewis et al. |
| 5,622,985 A | 4/1997 | Olukotun et al. |
| 5,634,895 A | 6/1997 | Igo et al. |
| 5,643,944 A | 7/1997 | Garfield et al. |
| 5,648,101 A | 7/1997 | Tawashi |
| 5,650,418 A | 7/1997 | Rath et al. |
| 5,665,077 A | 9/1997 | Rosen et al. |
| 5,681,278 A | 10/1997 | Igo et al. |
| 5,681,819 A | 10/1997 | Tang et al. |
| 5,686,104 A | 11/1997 | Mills et al. |
| 5,693,614 A | 12/1997 | Torii et al. |
| 5,712,396 A | 1/1998 | Magnin et al. |
| 5,723,456 A | 3/1998 | Jirousek et al. |
| 5,741,776 A | 4/1998 | Clark et al. |
| 5,756,453 A | 5/1998 | Vedder et al. |
| 5,767,160 A | 6/1998 | Kaesemeyer |
| 5,788,987 A | 8/1998 | Busetti et al. |
| 5,789,422 A | 8/1998 | Reichard et al. |
| 5,795,898 A | 8/1998 | Brown et al. |
| 5,811,416 A | 9/1998 | Chwalisz et al. |
| 5,824,331 A | 10/1998 | Usala |
| 5,830,879 A | 11/1998 | Isner |
| 5,830,910 A | 11/1998 | Mattson |
| 5,852,058 A | 12/1998 | Cooke et al. |
| 5,861,168 A | 1/1999 | Cooke et al. |
| 5,874,471 A | 2/1999 | Waugh |
| 5,876,756 A | 3/1999 | Takada et al. |
| 5,882,682 A | 3/1999 | Rork et al. |
| 5,883,109 A | 3/1999 | Gregg et al. |
| 5,891,459 A | 4/1999 | Cooke et al. |
| 5,895,783 A | 4/1999 | Garfield et al. |
| 5,895,788 A | 4/1999 | Wideman, Jr. et al. |
| 5,898,038 A | 4/1999 | Yallampalli et al. |
| 5,900,433 A | 5/1999 | Igo et al. |
| 5,906,987 A | 5/1999 | Chwalisz et al. |
| 5,910,482 A | 6/1999 | Yallampalli et al. |
| 5,912,019 A | 6/1999 | Singh |
| 5,945,452 A | 8/1999 | Cooke et al. |
| 5,968,983 A | 10/1999 | Kaesemeyer |
| 5,977,107 A | 11/1999 | Cai et al. |
| 6,004,925 A | 12/1999 | Dasseux et al. |

| | | | | | |
|---|---|---|---|---|---|
| 6,007,824 A | 12/1999 | Duckett et al. | EP | 1721608 A2 | 11/2006 |
| 6,028,106 A | 2/2000 | Garfield et al. | EP | 1139753 B1 | 7/2007 |
| 6,028,107 A | 2/2000 | Waugh | JP | 60139621 A | 7/1985 |
| 6,040,147 A | 3/2000 | Ridker et al. | JP | 9183797 A | 7/1997 |
| 6,040,340 A | 3/2000 | Chwalisz et al. | WO | WO 84/02131 A1 | 6/1984 |
| 6,054,453 A | 4/2000 | Lohray et al. | WO | WO 90/11070 A1 | 10/1990 |
| 6,063,432 A | 5/2000 | Maxwell et al. | WO | WO 92/10188 A1 | 6/1992 |
| 6,093,719 A | 7/2000 | Bocan | WO | WO 92/11895 A1 | 7/1992 |
| 6,117,455 A | 9/2000 | Takada et al. | WO | WO 94/01006 | 1/1994 |
| 6,117,872 A | 9/2000 | Maxwell et al. | WO | WO 95/02408 | 1/1995 |
| 6,133,320 A | 10/2000 | Yallampalli et al. | WO | WO 95/05866 A1 | 3/1995 |
| 6,165,975 A | 12/2000 | Adams et al. | WO | WO 95/13063 A1 | 5/1995 |
| 6,174,548 B1 | 1/2001 | Chen et al. | WO | WO 95/13800 | 5/1995 |
| 6,180,597 B1 | 1/2001 | Liao | WO | WO 95/13802 | 5/1995 |
| 6,187,744 B1 | 2/2001 | Rooney | WO | WO 95/15753 | 6/1995 |
| 6,207,190 B1 | 3/2001 | Richardson et al. | WO | WO 95/22345 | 8/1995 |
| 6,207,713 B1 | 3/2001 | Fossel | WO | WO 96/00038 | 1/1996 |
| 6,210,700 B1 | 4/2001 | Valente et al. | WO | WO 96/00112 | 1/1996 |
| 6,235,311 B1 | 5/2001 | Ullah et al. | WO | WO 96/08286 A1 | 3/1996 |
| 6,239,172 B1 | 5/2001 | Kaesemeyer | WO | WO 98/08500 | 3/1998 |
| 6,251,457 B1 | 6/2001 | Takaichi et al. | WO | WO 98/11893 A1 | 3/1998 |
| RE37,314 E | 8/2001 | Hirai et al. | WO | WO 98/33494 | 8/1998 |
| 6,277,884 B1 | 8/2001 | de Tejada | WO | WO 98/43630 A1 | 10/1998 |
| 6,312,663 B1 | 11/2001 | Boykin, Jr. | WO | WO 98/47509 A1 | 10/1998 |
| 6,323,211 B1 | 11/2001 | Garvey et al. | WO | WO 99/18952 | 4/1999 |
| 6,328,979 B1 | 12/2001 | Yamashita et al. | WO | WO 99/47123 A1 | 9/1999 |
| 6,350,782 B1 | 2/2002 | Moretti | WO | WO 99/59433 | 11/1999 |
| 6,358,536 B1 | 3/2002 | Thomas | WO | WO 99/62509 A1 | 12/1999 |
| 6,359,007 B1 | 3/2002 | Pearson et al. | WO | WO 00/06151 A1 | 2/2000 |
| 6,365,184 B1 | 4/2002 | Depui et al. | WO | WO 00/20382 | 4/2000 |
| 6,391,895 B1 | 5/2002 | Towart et al. | WO | WO 00/23102 | 4/2000 |
| 6,423,751 B1 | 7/2002 | Liao | WO | WO 00/29033 | 5/2000 |
| 6,425,881 B1 | 7/2002 | Kaesemeyer | WO | WO 00/45651 A1 | 8/2000 |
| 6,436,997 B1 | 8/2002 | de Tejada | WO | WO 00/56328 A1 | 9/2000 |
| 6,475,521 B1 | 11/2002 | Timmins et al. | WO | WO 00/59304 | 10/2000 |
| 6,475,530 B1 | 11/2002 | Kuhrts | WO | WO 00/74701 A2 | 12/2000 |
| 6,485,941 B1 | 11/2002 | Waldrop et al. | WO | WO 00/74701 A3 | 12/2000 |
| 6,500,804 B2 | 12/2002 | Demuth et al. | WO | WO 00/74742 A1 | 12/2000 |
| 6,511,800 B1 | 1/2003 | Singh | WO | WO 01/15744 A1 | 3/2001 |
| 6,531,507 B1 | 3/2003 | Pflaum et al. | WO | WO 01/35953 A2 | 5/2001 |
| 6,537,987 B1 | 3/2003 | Kaufmann | WO | WO 01/60348 A1 | 8/2001 |
| 6,635,273 B1 | 10/2003 | Loscalzo et al. | WO | WO 01/74295 | 10/2001 |
| 6,652,838 B2 | 11/2003 | Weinstein et al. | WO | WO 01/78747 A1 | 10/2001 |
| 6,683,080 B2 | 1/2004 | Fryburg et al. | WO | WO 02/96883 A1 | 5/2002 |
| 6,692,764 B2 | 2/2004 | Katdare et al. | WO | WO 03/94909 A3 | 11/2003 |
| 6,693,094 B2 | 2/2004 | Pearson et al. | WO | WO 03/94909 A2 | 11/2003 |
| 6,699,904 B2 | 3/2004 | Hayward et al. | WO | WO 2004/037203 A3 | 5/2004 |
| 6,734,175 B2 | 5/2004 | Hadcock et al. | WO | WO 2004/037203 A2 | 5/2004 |
| 6,734,337 B2 | 5/2004 | Wakil et al. | WO | WO 2004/045651 A1 | 6/2004 |
| 6,818,669 B2 | 11/2004 | Moskowitz et al. | WO | WO 2005/035001 A1 | 4/2005 |
| 6,821,977 B2 | 11/2004 | Gammill | WO | WO 2006/081147 A1 | 8/2006 |
| 6,830,759 B2 | 12/2004 | Makino et al. | WO | WO 2006/124161 A1 | 11/2006 |
| 6,861,440 B2 | 3/2005 | Boehringer et al. | | | |
| 6,953,593 B2 | 10/2005 | Kuhrts | | | |
| 7,030,152 B1 | 4/2006 | Ridker et al. ......... 514/423 | | | |
| 7,381,731 B2 | 6/2008 | Kaesemeyer | | | |
| 2001/0056068 A1 | 12/2001 | Chwalisz et al. | | | |
| 2002/0034546 A1 | 3/2002 | Ullah et al. | | | |
| 2003/0078269 A1 | 4/2003 | Pearson et al. | | | |
| 2004/0180077 A1 | 9/2004 | Riker et al. | | | |
| 2004/0192702 A1 | 9/2004 | Zablocki et al. | | | |
| 2004/0224999 A1 | 11/2004 | Mann et al. | | | |
| 2004/0258674 A1 | 12/2004 | Jalili | | | |
| 2005/0038102 A1 | 2/2005 | Liao et al. | | | |
| 2005/0287210 A1 | 12/2005 | Ron | | | |
| 2005/0288373 A1 | 12/2005 | Ron | | | |
| 2006/0104941 A1 | 5/2006 | Ridker et al. | | | |
| 2008/0145424 A1 | 6/2008 | Ron | | | |

FOREIGN PATENT DOCUMENTS

| | | |
|---|---|---|
| EP | 1671630 A2 | 6/2006 |

OTHER PUBLICATIONS

Brown et al., Drugs Used in the Treatment of Hyperlipoproteinemias, Ch. 36 in Goodman & Gilman's The Pharmacological Basis of Therapeutics, 8th Edition, Gilman et al. (eds.), Pergamon Press, Elmsford, NY, 1990, only pp. 874 and 881–886.

Flodstrom et al., Expression of the Citrulline–Nitric Oxide Cycle in Rodent and Human Pancreatic β–Cells: Induction of Argininosuccinate Synthase by Cytokines, Endocrinology, 136(8), 3200–3206 (1995).

Schroeder et al., Nitric Oxide: Physiology and Pharmacology, Anesthesia & Analgesia, 81(5), 1052–1059 (Nov. 1995).

Ignarro, Louis J, 1991, Pharmacology of Endothelium–Derived Nitric Oxide and Nitrovasodilators, The Western Journal of Medicine, vol. 154, No. 1, pp. 51–52. Jan. 1991.

Stewart, D.D., 1888, Remarkable Tolerance to Nitroglyercin, Philadelphia Polyclinic, 171–172.

Freelisch et al., Biochem. and Biophy. Res. Comm. 1991: 180, No. 1: 286–293.

Wolf, Yehuda G. et al., Nitroglycerin decreases medial smooth muscle cell proliferation after arterial balloon injury, Journal of Vascular Surgery, Mar. 1995, p. 499–503, vol. 21, issue #3.

Keith, R.A.,. et al., JPET, 1982, 221: 525–531.

Robinson, Sustained Action Dosage Forms in The Theory and Practice of Industrial Pharmacy 2.sup.nd ed., Lachman et al eds., Ch. 14:439–465, 1976.

Gennaro ed., Remington's Pharmaceutical Sciences 18.sup.th ed., 1990, Mack Publishing Co., Easton, PA (Table of Contents.

Boylan et al. eds., Handbook of Pharmaceutical Excipients, 1986, Publ. by American Pharmaceutical Assoc., Washington, DC (Table of Contents).

Lieberman et al. eds., Pharmaceutical Dosage Forms, Tablets, 1990, Marcel Dekker Inc., New York, NY (Table of Contents).

Richman, D. et al. Preparation and Stability of glyceryl trinitrate sublingual tablets prepared by direct compression. Journal of Pharmaceutical Sciences 54, No. 3 (Mar. 1965): 447–51.

Isidori, et al. A study of growth hormone release in man after oral administration of amino acids. Current Medical Research and Opinion 7, No. 7 (1981): 475–81.

Smith, D. et al. Tissue plasminogen activator release in vivo in response to vasoactive agents. Blood 66, No. 4 (Oct. 1985): 835–39.

Shikano, K. et al. Endothelium–derived relaxing factor is a selective relaxant of vascular smooth muscle. J. Pharmacol. Exp. Ther. 243, No. 1 (1987): 55–60.

Vidal, M.J. et al. Endothelium–derived relaxing factor inhibits renin release. European Journal of Pharmacology 149 (1988): 401–02.

Carling, D. and Hardie D. The substrate and sequence specificity of the amp–activated protein kinase. Phosphorylation of glycogen synthase and hosphorylast kinase. (abstract) Biochim Biophys Acta 1012, No. 1 (Jun. 15, 1989): 81–86.

Boje, K and H. Fung. Endothelial nitric oxide generating enzyme(s) in the bovine aorta: subcellular location and metabolic characterization. J. Pharmacol. exp. Ther. 253, No. 1 (1990):20–26.

Dubois–Rande, J et al. Effects of infusion of L–arginine into the left anterior descending coronary artery on acetylcholine–induced vasocontriction of human theromatous coronary arteries. Am. J. Cardiol 70 (1992): 1269–75.

Gray, D. and I Marshall. Nitric oxide synthesis inhibitors attenuate calcitonin gene–related peptide endothelium–dependent vasorelaxation in rat aorta. European Journal of Pharmacology 212 (1992): 37–42.

Jezdimirovic, M. et al. The effects of L–arginine of N.sup. G–nitrol–1–arginine methyl ester (L–NAME) on tolerance to nitroglycerol and cyclic gmp accumulation in the isolated bovine abdominal aorta. Acta Veterinaria (Beograd) 42, 2–3 (1992): 153–60.

Ashmarina, L.I. et al. 3–Hydroxy–3–methylglutaryl–CoA Lyase is present in mouse and human liver peroxisomes. Journal of Biological Chemistry 269, No. 50 (1994): 31929–32. [abstract only].

Furberg, C. et al. Effect of lovastatin on early carotid atherosclerosis and cardiovascular events. Circulation 90, No. 4 (Oct. 1994): 1679–87. [abstract only].

Hendrikx, M. et al. New Na+–H+ exchange inhibitor HOE 694 improves postichemic function and high–energy phosphate resynthesis and reduces Ca.sup.2+ overload in isolated perfused rabbit heart. Circulation 89, No. 6 (Jun. 1994): 2787–98. [abstract only].

Morris, K.R. et al. An integrated approach to the selection of optimal salt form for a new drug candidate. International Journal of Pharmaceutics (Amsterdam) 105, No. 3 (1994): 209–17. [abstract only].

Cynober, L et al. Arginine metabolism in mammals. J. Nutr. Biochem. 6 (Aug. 1995): 402–13.

Feelisch, M. et al. Human endothelial cells bioactivate organic nitrates to nitric oxide: implications for the reinforcement of endothelial defence mechanisms. European Journal of Clinical Investigation 25 (1995): 737–745.

Hiramatsu, T et al. Effects of L–arginine and L–nitro–arginine methyl ester on recovery of neonatal lamb heats after cold–ischemia. (abstract) J. Thorac. Cardiovasc. Surg. 109, 1(Jan. 1995): 81–87. [abstract only].

Jukema, J et al. Effects of lipid lowering by pravastation on progression and regression of coronary artery disease in symptomatic men with normal to moderately elevated serum cholesterol levels. Circulation 91 (1995): 2528–40. [abstract only].

Patel, J.and E. Block. Sulfhydryl–disulfide modulation and the role of disulfide oxidoreductases inregulation of the catalytic activity of nitric oxide synthase in pulmonary artery endothelial cells. Am. J. Respir. Cell. Mol. Bio. 13 (1995): 352–59.

Tsuda, Y. et al. Effects of pravastatin sodium and simvastatin on plasma fibrinogen level and blood rheology in type II hyperlipoproteinemia. Atherosclerosis 122 (1996): 225–33.

Ceremuzynski, L et al. L–Arginine improves exercise capacity in patients with stable angina (abstract). JACC 962–94 (Feb. 1997): 157A.

Wascher, T. et al. Vascular effects of L–arginine: anything beyond a substrate for the NO–Synthase? Biochemical and Biophysical Research Communications 234, No. 1 (1997): 35–38.

Sellke et al., Enhanced microvascular relaxations to VEGF and bFGF in chronically ischemic porcine myocardium, 271 (2 pt 2) H713–20, Aug. 1996.

Cuevas, P., Hypotensive Activity of Fibroblast Growth Factor, Science, vol. 254, pp. 1208–1210, Nov. 22, 1991.

Bouck, N. et al. How Tumors Become Angiogenic. Advances in Cancer Research 1996; 69:136–174.

Drexler, H. et al. Correction of Endotelial Dysfunction in Coronary Microcirculation of Hypercholesterolaemia Patients by L–Arginine. The Lancet. vol. 338 pp. 1546–1550. Dec. 21/28, 1991.

Lee, T. J. F. et al. Inhibition of Cerebral Neurogenic Vasolidation by L–Glutamine and Nitric Oxide Synthase Inhibitors and Its Reversal by L–Citruline. The Journal of Pharmacology and Experimental Therapeutics. vol. 276, No. 2. pp. 353–358. 1996.

Horn, M. et al. Preservation of Left Ventricular Mechanical Function and Energy Metabolism in Rats After Myocardial infarction by the Angiotesin–Converting Enzyme Inhibitor Quinapril. [Abstract Only] Journal of Cardiovascular Pharmacology. vol. 27. p. 201–210. 1996.

Quigley, R. L. et al. Immediate Hemodynamic Effects of Thrombolytic Therapy on the Ischemic Myocardium. Catherization and Cardiovascular Diagnosis, vol. 38. pp. 325–330. 1996.

Abou–Mohamed, G. et al. L–Arginine in the Development and Reversal of Tolerance to Nitroglycerine. (Abstract Only) FASEB J. vol. 10, No. 3. p. A569(No. 3280) 1996.

Edner, M. et al. Effect of Enalapril Initiated Early after Acute Mycardial Infarction on Heart Failure Parameters, with Reference to Clinical Class and Echocardiographic Determinants. Clin. Cardiol. vol. 19, pp. 543–548. 1996.

Saavedra, J. E. et al. Localizing Antithrombolic and Vasodilatory Activity with a Novel, Ultrafast Nitric Oxide Donor. Journal of Medicinal Chemistry. vol. 39, No. 22. pp. 4361–4365. 1996.

Mori, K. et al. Endothelium–Dependent Relaxation of Rat Thoracic Aorta by Amrinone–Induced Nitric Oxide Release. Eur. Heart J, 17: 308–316, 1996.

Schwarzacher, S. P. et al. Local Delivery of L–Arginine Increases Vascular Nitric Oxide Production and Improves Endothelium Dependent Vasomotion. (Abstract Only) JACC. No. 779–6. p. 288A Feb. 1996.

Fayyaz, M. et al. Antioxidants Are Vasodilators. JACC. No. 933–88. p. 130A. Feb. 1996.

Daghigh, F. et al. Chemical Modification and Inactivation of Rat Liver Arginase by N–Bromosuccinimide: Reaction with His141. Archives of Biochemistry & Biophysics. vol. 327. pp. 107–112. Mar. 1, 1996.

Xabregas, A. et al. Nitric Oxide, L–Arginine, Hypertension and Cardiopulmonary Bypass Three Case Reports. Applied Cardiopulmonary Pathophysiology. vol. 5. pp. 231–236. 1995.

Castillo, L. et al. Plasma Arginine, Citrulline, and Omithine Kinetics in Adults, with Observations on Nitric–Oxide Synthesis. (Abstract Only) American Journal of Physiology–Endocrinology and Metabolism. vol. 31, No. 2. pp. E 360–E 367. Feb. 1995.

Hecker, M. et al. Inhibition of Arginase by NG–Hydroxy–L–Arginine in alveolar macrophages: Implications for the Utilization of L–Arginine for Nitric Oxide Synthesis. FEBS Letters. vol. 359(2–3). pp. 251–254. Feb. 13, 1995.

Yu, Y. M. et al. Plasma Arginine and Leucine Kinetics and Urea Production Rates in Burn Patients. (Abstract Only) Metabolism–Clinical and Experimental. vol. 44. No. 5. pp. 659–666. May 1995.

Beaumier, L. et al. Urea Cycle Intermediate Kinetics and Nitrate Excretion at Normal and Therapeutic Intakes of Arginine in Humans. (Abstract Only) American Journal of Physiology–Endocrinology and Metabolism. vol. 32. No. 5. pp. E 884–E 896. Nov. 1995.

Sessa, W. C. the Nitric Oxide Synthase Family of Proteins. J Vasc Res. vol. 31. pp. 131–143. 1994.

Cloaree–Blanchard, L. et al. Rapid Development of Nitrate Tolerance in Healthy Volunteers: Assessment Using Spectral Analysis of Short–Term Blood Pressure and Heart Rate Variability. (Abstract Only) Journal of Cardiovascular Pharmacology. vol. 24. pp. 266–273. 1994.

Celermajer, D. S. et al. Role of Endothelium in the Maintenance of Low Pulmonary Vascular Tone in Normal Children. Circulation. vol. 89(5). pp. 2041–2044. 1944.

Boesgaard, S. et al. Nitrate Tolerance in Vivo Is Not Associated With Depletion of Arterial of Venous Thiol Levels. Circulation Research. vol. 74, No. 1. pp. 115–120. Jan. 1994.

Hrabak, A. et al. Comparison of Substrate and Inhibitor Specificity of Arginase and Nitric Oxide (NO) Synthase for Arginine Analogues and Related Compounds in Murine and Rat Macrophages. Biochemical & Biophysical Research Communications. vol. 198(1). pp. 206–212.Jan. 14, 1994.

Fujita, H. et al. The Improved Myocardial Perfusion By L–Arginine in Patients with Vasospastic Angina. (Abstract Only) JACC. Abstracts No. 877–22. p. 201A. Feb. 1994.

Faraci, F. M. et al. Nitric Oxide and the Cerebral Circulation. Stroke. vol. 25, No. 3. pp. 692–702. Mar. 1994.

Dreler, H. et al. Effect of L–Arginine on Coronary Endothelial Function in Cardiac Transplant Recipients. Circulation. vol. 89, No. 4. pp. 1615–1623. Apr. 1994.

Fuentes, J. M. et al. Kinetics of Manganese Reconstruction and Thiol Group Exposition in Dialyzed Rat Mammary Gland Arginase. International Journal of Biochemistry. vol. 26(15). pp. 653–659. May 1994.

Daghigh, F., et al. The Plasma Flux and Oxidation Rate of Omithine Adaptively Decline with Restricted with Restricted Arginine Intake. Proceedings of the National Aadamy of Sciences of the United State of America. vol. 91, No. 14. pp. 6393–6397. Jul. 1994.

Fukuto, D. F. et al. Inhibition of Rat Liver Arginase by an Intermediate in NO Biosynthesis, NG–Hydroxyl–L–Arginine: Implications for the Regulation of Nitric Oxide Biosynthesis by Arginase. (Abstract Only) Biochemical & Biophysical Research Communication. vol. 202(1). pp. 174–180. Jul. 15, 1994.

Reczkowski, R. S. et al. Rat Liver Arginase: Kinetic Mechanism, Alternate Substrates, and Inhibitors. (Abstract Only) Archives of Biochemistry & Biophysics. vol. 312(1). pp. 31–37. Jul. 1994.

Kumagai, K. et al. Nitric Oxide Increases Renal Blood Flow by Interacting With the Sympathetic Nervous System. Hypertension. vol. 24, No. 2. pp. 220–226. Aug. 1994.

Anderson, T. J. et al. Nitric Oxide and Nitrovasodilators: Similarities, Differences and Potential Interactions. JACC. vol. 24, No. 2, pp. 555–566. Aug. 1994.

Boucher, J. L. et al. N Omega–Hydroxyl–L–Arginine, An Intermediate in the L–Arginine to Nitric Oxide Pathway, is a Strong Inhibitor of Liver and Macrophage Arginase. Biochemical & Biophysical Research Communications. vol. 203(3). pp. 1614–1621. Sep. 30, 1994.

Lind, D. S. et al. Endotoxin Stimulates Arginine Transport in Pulmonary Artery Endothelial Cells. (Abstract Only) Surgery. vol. 114. pp. 199–205. 1993.

Kawata, H. et al. Nitroglycerin Improves Functional Recovery of Neonatal Lamb Hearts After 2 Hours of Cold Ischemia. (Abstract Only) Circulation. vol. 88[part 2]. pp. 366–371. 1993.

Feelisch, M. Biotransformation to Nitric Oxide of Organic Nitrates in Comparison to Other Notrovasodilators. European Heart Journal. vol. 14 [Supp. 1]. pp. 123–132. 1993.

De Garavilla, L. et al. lack of Cross–Tolerance Between Nitroglycerin and Endothelium–Derived Relaxing Factor–Mediated Vasoactive Agents in Spontaneously Hypertensive Rats. European Journal of Pharmacology. vol. 234. pp. 77–82. 1993.

Castillo, L. et al. Splanchnic Metabolism of Dietary Arginine in Relation to Nitric–Oxide Synthesis on Normal Adult Man. Proceedings of the National Academy of Sciences of the United States of America. vol. 90, No. 1. pp. 193–197. Jan. 1, 1993.

Quyyumi, A. A. et al. Effect of L–Arginine, the Substrate for Nitric Oxide, on Endothelium–Dependent Vasodillation of the Coronary Microvasculature. (Abstract Only) JACC. Abstract No. 883–52. vol. 21, No. 2. p. 151 A. Feb. 1993.

Dinerman, J. L. et al. Molecular Mechanisms of Nitric Oxide Regulation. Circulation Research. vol. 73, No. 2. pp. 217–222. Aug. 1993.

Kitamura, Y. et al. Nitric Oxide–Mediated Retinal Arteriolar and Arterial Dilatation Induced by Substance P. Investigative Ophthalmology & Visual Science. vol. 34, No. 10. pp. 2859–2865. Sep. 1993.

Mehta, J. L. et al. Free Radicals, Antioxidants, and Coronary Heart Disease. The Journal of Myocardia Ischemia. vol. 5, No. 8. pp. 31–33, 37–41. Sep. 1993.

Robertson, C. A. et al. Effect of Nitric Oxide Synthase Substrate Analog Inhibitors on Rat Liver Arginase. Biochemical & Biophysical Research Communications. vol. 197(2). pp. 523–528. Dec. 15, 1993.

Marletta, M. A. Nitric Oxide, Nitrovasodilators and L–Arginine–An Unusual Relationship. Western Journal of Medicine. vol. 154, No. 1. pp. 107–109. Jan. 1991.(abstract).

Feelisch, M. et al. Biotransformation of Organic Nitrates to Nitric Oxide By Vascular Smooth Muscle and Endothelial Cells. Biochemical and Biophysical Research Communications, vol. 180, No. 1. pp. 286–293. Oct. 15, 1991.

Zembowicz, A. et al. Nitric Oxide and Another P)otent Vasodilator are Formed Ng–Hydroxy–L–Arginine by Cultured Endothelial Cells. Proc. (Abstract Only) Natl. Acad. Sci. USA. vol. 88. pp. 11172–11176. Dec. 1991.

Schroder, H. et al. Cross–Tolerance to L–Arginine Dependent Guanylate Cyclase Activators in Nitrate–Tolerant LLC–PK Kidney Epithelial Cells. Pol. J. Pharmacol. Pharm. vol. 42. pp. 259–263. 1990.

Verdemikov, Y. P. et al. Endothelium–Derived Relaxing Factor is Not Identical to Nitric Oxide. Nitric Oxide From L–Arginine: A bio–Regulatory System. Elsevier Science Publishers. Chap. 39. pp. 373–377. 1990.

Yang, Z. et al. Endothelium–Derived Nitric Oxide in Human Arteries and Veins. Nitric Oxide From L–Arginine: A bio–Regulatory System Elsevier Science Publishers. Chap. 11. pp. 89–93. 1990.

Sakuma, I. et al. L–Arginine is a Precursor of Endothelium–Derived Relaxing Factor in Various Animal Species and Vascular Beds. Nitric Oxide From L–Arginine: A bio–Regulatory System. Elsevier Science Publishers. Chap. 49. pp. 445–449. 1990.

Sneddon, J. M. et al. Transport and Metabolism of L–Arginine by Bovine Aortic endothelial Cells. Nitric Oxide From L–Arginine: A bio–Regulatory System. Elsevier Science Publishers. Chap. 51. p. 457(Intro Only). 1990.

Smith, R.E.A. et al. Role of Nitric Oxide Synthesis in the Regulation of Coronary Vascular Tone in the Isolated Perfused Rabbit Heart. Cardiovascular Research. vol. 26, pp. 508–512. 1992.

Nakanishi, K. et al. Intracoronary L–Arginine Reperfusion Improves Endothelial Function and Reduces Infarct Size. Am. J. Physiol. pp. H1650–H1658. 1992.

Morikawa, E. et al. L–Arginine Decreases Intact Size Caused By Middle Cerebral Arterial Occlusion in SHR. American Journal of Physiology. vol. 263(5 pt. 2). pp. H1632–H1635. 1992.

Mayhan, W. G. et al. Acetylcholine Induces Vasoconstriction in the Microcirculation of Cardiomyopathic Hamsters: Reversal By L–Arginine. Biochemical and Biophysical Research Communications vol. 184, No. 3. pp. 1372–1377. May 15, 1992.

Weyrich, A. S. et al. The Role of L–Arginine in Ameliorating Reperfusion Injury After Myocardial Ischemia iin the Cat. Circulation. vol. 86. No. 1. pp. 279–287. Jul. 1992.

Dinerman, J. L. et al. Interactions Between Nitroglycerin and Endothelium in Vascular Smooth Muscle Relaxation. Am. J. Physiol. vol. 26. pp. H698–H701. 1991.

Richard, V. et al. The L–Arginine–Nitric Oxide Pathway in the Canine Femoral Vascular Bed: In Vitro and In Vivo Experiments. Fundam. Clin. Pharmacol. vol. 5, pp. 777–788. 1991.

Schor, K. et al. Generation of Nitric Oxide from Organic Nitrovasodilators During Passage Through the Coronary Vascular Bed and Its Role in Coronary Vasodilation and Nitrate Tolerance. Blood Vessels. vol. 38. pp. 62–66. 1991.

Boesgard, S. et al. Nitrat tolerance: Effect of Thio supplementation during prolonged nitroglycerin infusion in an in vivo rat model JPET. vol. 258, pp. 851–855. 1991.

Schini, V. B. et al. L–Arginine Evokes Both Endothelium–Dependant and Independant Relaxations in L–Arginine–Depleted Aortas of the Rat. (Abstract Only) Circulation Research. vol. 68. pp. 209–216. 1991.

Gold, M.E. et al. L–Arginine–Dependent Vascular Smooth Muscle Relaxation and cGMP Formation. Am. J. Physiol. vol. 259. pp. H1813–H1821. 1990.

Bredt, D.S. et al. Isolation of Nitric Oxide Synthetase, A Calmodulin–Requiring Enzyme. Proc. Natl. Acad. Sci. USA. vol. 87. pp. 682–685. Jan. 1990.

Nakaki, T. et al. L–Arginine–Induced Hypotension. The Lancet. p. 696. Sep. 15, 1990.

Bennett, B.M. et al. Relationship Between Biotransformation of Glyceryl Trintrate and Cyclic GMP Accumlation in Various Cultured Cell Lines. The Journal of Pharmacology and Experimental Therapeutics. vol. 250, No. 1. pp. 316–322. 1989.

Gold, M.E. et al. Depletion of Arterial L–Arginine Causes Reversible Tolerance to Endothelium–Dependant Relaxation. Biochemical and Biophysical Research Communications. vol. 164, No. 2. pp. 714–721. Oct. 31, 1989.

Bredt, D.S. et al. Nitric Oxide Mediates Glutamate–Linked Enhancement of cGMP Levels in the Cerebellum. Proc. Natl. Acad. Sci. USA. vol. 86. pp. 9030–9033. Nov. 1989.

Arginine Hydrochloride. American Hosp. Form. Drug Inf. Dir. pp. 1314–1315. 1988.

Palmer, R. M. J. et al. Vascular Endothelial Cells Synthesize Nitric Oxide From L–Arginine. Nature. vol. 333. pp. 664–666. Jun. 16, 1988. (abstract).

Flaherty, J. T. Comparison of Intravenous Nitroglycerin and Sodium Nitroprusside in Acute Myocardial Infarction. The American Journal of Medicine. pp. 53–60, Jun. 27, 1983.

Currie, G. A. Activated Macrophages Kill Tumor Cells by Releasing Arginase. Nature. vol. 273. pp. 758–759. Jun. 29, 1978.

Flaherty, J. T. et al. Intravenous Nitroglycerin in Acute Myocardial Infarction. Circulation. vol. 51. pp. 132–139. Jan. 1975.

Parker, M. L. et al. The Arginine Provocative Test: An Aid in the Diagnosis of Hyposematotrepism. J. Clin. Endo. vol. 27. pp. 1129–1136. Aug. 1967.

Knopf, et al. Plasma Growth Hormone Response to Intravenous Administration of Amino Acids.Preliminary Communication . vol. 25. pp. 1140–1144. Aug. 1965.

Persson, M.G. et al. Nitric Oxide—More Than a Vasodilator. (Abstract Only) Lakartidningen, vol. 90, No. 14. pp. 1365–1371. Apr. 7, 1993.

Chen, R.Y. et al. Role of L–Arginine–Derived Nitric Oxide in Cholinergic Dilation of Gastric Arterioles. (Abstract Only) Am J. Physiol. vol. 265, No. 6, pt. 2. p. H2110–6. Dec. 1993.

Parent R. et al. Contribution of Nitric Oxide to Dilation of Resistance Coronary Vessels in Conscious Dogs. Am. J. Physiol. vol. 262, No. 1, pt. 2. p. H10–6. Jan. 1992.

Waldman et al. Cyclic GMP synthesis and function. Pharmacol. Rev., 1987, vol. 39, 163.

Bogaert, M. Clinical relevance of tolerance to nitrovasodilators, J. Cardiovas. Pharmacol., 1991, vol. 17 (3), S313.

Unger, P. et al. Tolerance to intravenous nitrates.J. Cardiovasc. Pharmacol., 1991, vol. 17 (3), S300.

Henry P. J. et al. S–Nitrosothiols as vasodilators: Implications regarding tolerance to nitric–oxide–containing vasodilators. Br. J. Pharmacol., 1989, vol. 98, 757.

Axelsson, K. L. et al. Nitrate tolerance from a biochemical point of view. Drugs, 1987, vol. 33, 63.

Levine B et al. Elevated circulating levels of tumor necrosis factor in severe chronic heart failure. NEJM, 1990, vol. 323, 236–241.

Fung H.L. Journal of Pharmacology and experimental Therapeutics, 1988, vol. 245 (2), 524–30.

Munzel T., et al. What Causes Nitroglycerin Tolerance?. Clin Cardiol Primary Cardiol 1994; 20:40–7.

Walter Sneader: Drug prototypes and their exploitation, 1995, John Wiley and Sons LTD. p. 567.

Isner et al., Clinical evidence of angiogenesis after arterial gene transfer of phVEGF165 in patient with ischaemic limb. Lancet. Aug. 10, 1996, vol. 348, No. 9024, Aug. 10, 1996, pp. 370–374.

Finder J et al., TGF –beta regulates production of NO in pulmonary artery smooth muscle cells by inhibiting expression of NOS . American Journal of Physiology, (May 1995) 268 (5 PT 1) L862–7.

Stroes Erik S G et al., Vascular function in the forearm of hypercholesterolaemic patients off and on lipid–lowering medication. Lancet (North American Ed.), vol. 346, No. 8973, 1995, pp. 467–471.

O'Driscoll Gerard et al., Simvastatin? an HMG–coenzyme A reduclase inhibitor, improves endothelial function within 1 month. Circulation, vol. 95, No. 5, 1997, pp. 1126–1131.

Luscher T F et al., Lipids And Endothelial Function—Effects Of Lipid–Lowering And Other Therapeutic Interventions. Current Opinion in Lipidology, (Aug. 1996) vol. 7, No. 4, pp. 234–240.

Lefer A M et al., Decreased basal nitric oxide release in hypercholesterolemia increases neutrophil adherence to rabbit coronary artery endothelium. Arteriosclerosis And Thrombosis: A Journal Of Vascular Biology / American Heart Association. United States Jun. 1993, vol. 13, No. 6, Jun. 1993 (Jun. 1993), pp. 771–776. (abstract).

Ridker P.M. et al., Inflammation, Aspirin, and the Risk of Cardiovascular Disease in Apparently Healthy Men The New England Journal Of Medicine vol. 336, No. 14, Apr. 3, 1997, pp. 973–979.

Buja L M. Does atherosclerosis have an infectious etiology? Circulation 1996; 94:872–873.

Haverkate, F., et al., Production of C–Reactive Protein and Risk of Coronary Events in Stable and Unstable Angina, Lancet, (1997), 349:462–466.

Lagrand, W.K., et al., C–Reactive Protein Colocalizes with Complement in Human Hearts During Acute Myocardial Infarction, (1997), Circulation, 95:97–103 (abstract).

Paul M. Ridker et al., Plasma concentration of soluble intercellular adhesion molecule 1 and risks of future myocardial infarction in apparently healthy men, The Lancet, vol. 351, No. 9096, pp. 88–92, Jan. 10, 1988.

Mendall et al, C Reactive protein and its relation to cardiovascular risk factors a population based cross sectional study, BMJ, vol. 312, pp. 1065–1069, Feb. 1996.

Russell P Tracy et al., Relationship of C–Reactive Protein to Risk of Cardiovascular Disease in the Elderly, Arteriosclerosis, Thrombosis, and Vascular Biology, vol. 17, No. 6 pp. 1121–1127, Jun. 1997.

Paul M Ridker et al., Plasma Concentration of C–Reactive Protein and Risk of Developing Peripheral Vascular Disease, Circulation, vol. 97, pp. 425–428, 1998.

Paul M. Ridker et al., C–Reactive Protein Adds to the Predictive Value of Total and HDl Cholesterol in Determining Risk of First Myocardial Infarction, Circulation, vol. 97, pp. 2007–2011, 1998.

Wolfgang Koenig, M.D., C–Reactive Protein, a Sensitive Marker of Inflammation, Predicts Future Risk of Coronary Heart Disease in Initially Healthy Middle–Aged Men, Circulation, vol. 99, pp. 237–242, 1999.

Paul M. Ridker et al., Prospective Study of C–Reactive Protein and the Risk of Future Cardiovascular Events Among Apparently Healthy Women, Circulation, vol. 98, pp. 731–733, 1998.

Paul M. Ridker et al., Inflammation, Pravastatin, and the Risk of Coronary Events After Myocardial Infarction in Patients With Average Cholesterol Levels, Circulation, vol. 98, pp. 839–844, 1998.

Giovanna Liuzzo, M.D. et al., The Prognostic Value of C–Reactive Protein and Serum Amyloid A Protein in Severe Unstable Angina, The New England Journal of Medicine, vol. 331; No. 7, pp. 417–424, Aug. 18, 1994.

Attilio Maseri, M.D. et al., Inflammation, Atherosclerosis, and Ishemic Events—Exploring The Hidden Side of the Moon, The New England Journal of Medicine, vol. 336, No. 14, pp. 1014–1016, Apr. 3, 1997.

Shi–Jen Hwang, et al., Circulating Adhesion Molecules VCAM–1, ICAM–1, and E–selectin in Carotid Atherosclerosis and Incident Coronary Heart disease Cases, Circulation, vol. 96, pp. 4219–4225, 1997.

Haverkate F., et al., C–reactive protein and cardiovascular disease, Fibrinolysis & Proteolysis, 11 (Suppl. 1), pp. 133–134, 1997 Biosis Abstract.

Di Minno G., Platelets, Prostaglandins and Thromboses. G. Arterioscler, 3(2), pp. 101–109, 1979, Biosis Abstract.

Patel P. Mendall MA, Carrington D, et al. Association of helicobacter pylori and chlamydia pneumoniae infections with coronary heart disease and cardiovascular risk factors. Br Med J 1995;311:711–4.

Steering Committee of the Physicians' Health Study Research Group. Final report of the aspirin component of the ongoing Physicians' Health Study. NEJM 321:129–35, 1989 (abstract).

Hennekens CH, Buring JE, Manson JE, et al. Lack of effect of long–term supplementation with beta carotene on the incidence of malignant neoplasms and cardiovascular disease. N Engl J Med 1996;334:1145–9.

Macy EM, Hayes TE, Tracy RP. Variability in the measurement of C–reactive protein in healthy adults: implications for reference interval and epidemiologic methods. Clin Chem 1997; 43–52–58.

Stampfer MJ, Sacks FM, Salvini S, Willett WC, Hennekens CH. A prospective study of cholesterol, apolipoproteins, and the risk of myocardial infarction. N Engl J Med 1991;325:373–81.

Ridker PM, Hennekens CH, Stampfer MJ. A prospective study of lipoprotein(a) and the risk of myocardial infarction. JAMA 1993;270:2195–2199.

Ridker PM, Vaughan DE, Stampfer MJ, Manson JE, Hennekens CH. Endogenous tissue–type plasminogen activator and risk of myocardinal infarction, Lancet 1993; 341:1165–1168.

Ridker PM, Hennekens CH, Cerskus A, Stampfer MJ. Plasma concentration of cross–linked fibrin degradation product (d–Dimer) and the risk of future myocardial infarction among apparently healthy men. CIrculation 1994;90: 2236–2240.

Das I. Raised C–reactive protein levels in serum from smokers. Clinica Chimica Acta 1985; 153:9–13.

Buja LM. Does atherosclerosis have an infectious etiology? Circulation 1996; 94:872–873.

Grayston JT. Chlamydia in atherosclerosis. Circulation 1993;87:1408–1409.

Saikku P, Leinonen M, Tenkanen L, et al. Chronic chlamydiapneumoniae infection as a risk factorfor coronary heart disease in the Helsinki Heart Study. Ann Intern Med 1992; 116:273–278.

Thorn DH, Grayston JT, Siscovick DS, Wang S–P, Weiss NS, Dating JR. Association of prior infection with chlamydia pneumoniae and angiographically demonstrated coronary artery disease. JAMA 1992;268:68–72.

Melnick JL, Adam E, DeBakey ME. Possible role of cytomegalovirus in atherogenesis. JAMA 1990;263;2204–7.

Mendall MA, Goggin PM, Molineaux N, et al. Relation of helicobacter pylori infection and coronary heart disease. Br Heart J 1994;71;437–9.

Bataille R, Klein B. C–reactive protein levels as a direct indicator of interleukin–6 levels in humans in vivo. Arthritis and Rheumatism 1992;35: 982–984.

Biasucci LM, Vitelli A, Liuzzo G, et al. Elevated levels of interleukin–6 in unstable angina. Circulation 1996;94:874–877.

Cermak J, Key NS, Bach RR, et al. C–reactive protein induces human peripheral blood monocytes to synthesize tissue factor. Blood 1993;82: 513–20.

Paul, William. Fundamental Immunology, 3rd edition, 1993. Raven Press, p. 1019–1027.

The Bantam Medical Dictionary, Revised Edition, 1990, p. 379.

Hackman et al., Levels of soluble cell adhesion molecules in patients with dyslipidemia, 93: 1334–1338, 1996. Circulation, 1996.

L.H. Kuller, et al., Relation of C–Reactive Protein and Coronary Heart Disease in the MRFIT Nested Case–Control Study, Am J Epidemiology, (1996), 144:537–547.

Hokanson et al., Plasma triglyceride level is a risk factor for cardiovascular disease independent of high density lipoprotein cholesterol level: a Meta–Analysis of Population–Based Prospective Studies, J. Cardiovasc. Risk, 1996, vol. 3, pp. 213–219.

Boushey et al., A quantitative assessment of Plasma Homocysteine as a Risk Factor for Vascular Disease. Probable Benefits of Increasing Folic Acid Levels, JAMA, 1995, vol. 274, pp. 1049–1057.

Tracy, Russell P., C–Reactive Protein and Incidence of Cardiovascular Disease in Older Women: the Rural Health Promotion Project and the Cardiovascular Health Study, Abstract, Circulation, (Feb. 1, 1996) 93 (3):622.

S. Thompson, et al., Hemostatic Factors and the Risk of Mycardial Infarction or Sudden Death in Patients with Angina Pectoris, 1995, The New England Journal of Medicine, vol. 332, No. 10, pp. 635–641.

Ridker P M, Hennekens C H, Selhub J, Miletich J P. Malinow M R, Stampfer M J. Interrelation of hyperhomocyst(e) inemia, factor V Leiden, and risks of future venous thromboembolism. Circulation 1997; 95(7): 1777–82.

Blauw, G.J., et al., Stroke, Statins, and Cholesterol: A meta–Analysis of Randomized, Placebo–Controlled, Double–Blind Trials With HMG–CoA Reductase Inhibitors, Stroke 28(5):946–950 (1997).

Casino, P.R., et al., The Role of Nitric Oxide in Endothelium–Dependent Vasodilation of Hypercholesterolemic Patients, Circulation 88(6): 2541–2547 (1993), Abstract.

Cooke, J.P., et al., Nitric Oxide Synthase: Role in the Genesis of Vascular Disease, Annu. Rev. Med. 48:489–509 (1997), Abstract.

Crouse, J.R., et al., Reductase Inhibitor Monotherapy and Stroke Prevention, Arch. Intern. Med. 157:1305–1310 (1997).

Glaid, A., et al., Reduced Expression of Endothelial Nitric Oxide Synthase in the Lungs of Patients with Pulmonary Hypertension, New Eng. J. Med. 333(4):214–221 (1995).

Hebert, P.R., et al., Cholesterol–Lowering Reduces Risks of Stroke and Total Mortality, Circulation 94 Suppl 1:I–744 (1996) Abstract 4351.

Jessup, W., Oxidized Lipoproteins and Nitric Oxide, Curr. Opin. Lipidol. 7(5):274–280 (1996), Abstract.

Laufs, U., et al., Neue Erkenntnisse uber die Wirkung von HMG–CoA–Reduktase–Hemmem, Dtsch. Med. Wschr. 122: 1255–1259 (1997).

Macdonald, P., et al., The Role of Nitric Oxide in Heart Failure. Potential for Pharmacological Intervention, Drugs Aging 8(6):452–458 (1996), Abstract.

Martinez–Riera, A., et al., Primary Prevention of Stroke, New Engl. J. Med. 334(17):1138–1139 (1996).

Massoudy, P. et al., Cardioprotection by Cyclosporine A in Experimental Ischemia and Reperfusion—Evidence for a Nitric Oxide–Dependent Mechanism Mediated by Endotheli, Mol. Cell Cardio. 29, 535–544 (1997).

Munzel, T., et al., The Physiology and Pathophysiology of the Nitric Oxide/Superoxide System, Herz. 22(3):158–172 (1997), Abstract.

Rector, T.S., et al., Randomized, Double–Blind, Placebo–Controlled Study of Supplemental Oral L–Arginine in Patients with Heart Failure, Circulation 93(12):2135–2141, 1996.

Stroes, E., et al., Tetrahydrobiopterin Restores Endothelial Function in Hypercholesterolemia, J. Clin. Invest. 99 (1):41–46 (1997), Abstract.

Wolf, A., et al., Dietary L–Arginine Supplementation Normalizes Platelet Aggregation in Hypercholesterolemic Humans J. Am. Coll. Cardiol. 29(3):479–485 (1997), Abstract.

Yokoyama, M., et al., Regulation of Nitric Oxide Synthase Gene Expression by Cytokines, J. Card. Fail. 2(4 Suppl): S179–S185 (1996), Abstract.

Dusting, G.J., Nitric Oxide in Coronary Artery Disease: Roles in Atherosclerosis, Myocardial Reperfusion and Heart Failure EXS 76:33–55 (1996).

Yano et al., Involvement of rho p21 in Cyclic Strain–Induced Tyrosine Phosphorylation of Focal Adhesion Kinase (pp125–FAK), Morphological Changes and Migration of Endothelial Cells, Biochemical and Biophysical Research Communications, vol. 224, pp. 508–515, (1996).

Herbert, P.R., et al., Cholesterol Lowering and the Risk of Stroke, Arch. Intern. Med. 156:214–215 (1996).

O'Driscoll et al., The HMG–CoA reductase inhibitor simvastatin improves endothelial function within one month Circulation, vol. 94, No. 8, 1996, p. I–401.

Casino, PR, The role of nitric oxide in endothelium–dependent vasodilation of hypercholesterolemic patients, Circulation, 1993; 88:2541–254.

Lerman, A., Inhibition of endothelium–derived relaxing factor enhances endothelin–mediated vasoconstriction, Circulation 1992; 85:1894–1898.

Treasure, Charles B., Beneficial Effects of Cholesterol–Lowering Therapy On The Coronary Endothelium In Patients With Coronary Artery Disease, New England J Med 1995; 332(8):481–487.

Anderson, Todd J., The Effect of Cholesterol–Lowering and Antioxidant Therapy on Endothelium–Dependent Coronary Vasomotion, New England J Med 1995; 332(8):488–493.

Shepherd, James, Prevention of Coronary Heart Disease With Pravastatin in Men with Hypercholesterolemia, New England J Med 1995: 333(20):1301–1307.

Guo, Jin–Ping, Direct measurement of nitric oxide release from vascular endothelial cells, J Appl Physiol 1996; 81(2):774–779.

Sacks, Frank M., The Effect of Pravastatin On Coronary Events After Myocardial Infarction in Patients With Average Cholesterol Levels, New England J Med 1996;335(14):1001–1009.

Scandinavian Simvastatin Survival Study Group, Randomised trial of cholesterol lowering in 4444 patients with coronary heart disease: the Scandinavian Simvastatin Survival Study (4S), Lancet 1994; 344: 1383–1389.

Levine, Glenn N., Cholesterol Reduction in Cardiovascular Disease, New England J Med 1995; 332(8):512–521.

Vaughan, Carl J., Statins do more than just lower cholesterol, Lancet 1996; 348:1079–1082.

Expert Panel on Detection, Evaluation, and Treatment of High Blood Cholesterol in Adults, Summary of the Second Report of the National Cholesterol Education Program (NCEP) Expert Panel on Detection, Evaluation, and Treatment of High Blood Cholesterol in Adults (Adult Treatment Panel II), JAMA 1993; 269(23):3015–3023.

Detection, Evaluation, and Treatment of High Blood Cholesterol in Adults (Adult Treatment Panel II), Circulation 1994; 89(3):1336–1445.

Detection, Evaluation, and Treatment of High Blood Cholesterol in Adults (Adult Treatment Panel II), National Institutes of Health 1993; 93–3095.

The West of Scotland Coronary Prevention Study Group, A Coronary Primary Prevention Study of Scottish Men Aged 45–64 Years: Trial Design, J Clin Epidemiol 1992; 45(8):849–860.

Vita, JA, Coronary vasomotor response to acetylcholine relates to risk factors coronary artery disease, Circulation 1990; 81:491–497.

Selke, FW, Endothelium–dependent vascular relaxation is abnormal in the coronary microcirculation of atherosclerotic primates, Circulation 1990; 81:1586–1593.

Harrison, DG, From isolated vessels to the catheterization laboratory, Studies of endothelial function in the coronary circulation of humans, Circulation 1989; 80:703–706.

Eichstädt, Hermann W., Improvement of Myocardial Perfusion by Short–Term Fluvastatin Therapy in Coronary Artery Disease, Am J Cardiol 1995; 76:122A–125A.

Schmieder, Roland E., Is Endothelial Dysfunction Reversible?, Am J Cardiol 1995; 76:117A–121A.

The LIPID Study Group, Design Features are Baseline Characteristics of the LIPID (Long–Term Intervention With Pravastatin in Ischemic Disease) Study: A Randomized Trial in Patients With Previous Acute Myocardial Infarction and/or Unstable Angina Pectoris, Am J Cardiol 1995; 76:474–479.

Carandente, Franca, Glossary of Chronobiology, Chronobiologia 1977; Suppl. 1:151–156.

Egashira, K et al., Reduction in Serum Cholesterol With Pravastatin Improves Endothelium–Dependent Coronary Vasomotion in Patients With Hypercholesterolemia, Circulation 1994;89:2519–2524.

Creager, Mark A. and Selwyn, Andrew, When 'Normal' Cholesterol Levels Injure the Endothelium, Editorial, Circulation, 1997;96:3255–3257.

Shear et al., Expanded Clinical Evaluation of Lovastatin (EXCEL) Study Results Effect of Patient Characteristics on Lovastatin–Induced Changes in Plasma Concentrations of Lipids and Lipoproteins, Circulation, 1992;85:1293–1303.

Chen, Z et al., Serum cholesterol concentration and coronary heart disease in population with low cholesterol concentrations, BMJ 1991:303:276–82.

Sacks F M et al., Rationale and Design of a Secondary Prevention Trial of Lowering Normal Plasma Cholesterol Levels After Acute Myocardial Infarction: The Cholesterol and Recurrent Events Trial (CARE) Am J Cardiol 1991;68:1436–1446.

Design and Baseline Results of the Scandinavian Simvastatin Survival Study of Patients with Stable Angina and/or Previous Myocardial Infarction, The Scandinavian Simvastatin Survival Study Group, Am J Cardiol 1993;71:393–400.

Armitage, Jane, Need for large scale randomized evidence about lowering LDL cholesterol in people with diabetes mellitus: MRC/BFH heart protection study and other major trials, Heart 2000; 84:357–360.

Heart Protection Study Collaborative Group, MRC/BHF Heart Protection Study of cholesterol lowering with simvastatin in 20 536 high–risk individuals: a randomized placebo–controlled trial, Lancet 2002; 360:7–22.

Ridker, Paul M., Rosuvastatin in the Primary Prevention of Cardiovascular Disease Among Patients With Low Levels of Low–Density Lipoprotein Cholesterol and Elevated High–Sensitivity C–Reactive Protein: Rationale and Design of the JUPITER Trial, Circulation 2003; 108:2292–2297.

Heart Protection Study Collaborative Group, MRC/BHF Heart Protection Study of cholesterol–lowering with simvastatin in 5963 people with diabetes: a randomized placebo–controlled trial, Lancet 2003; 361:2005–2016.

Laufs, Ulrich, Inhibition of 3–Hydroxy–3–methylglutaryl (HMG)CoA Reductase Blocks Hypoxia–mediated Down–regulation of Endothelial Nitric Oxide Synthase, J Biol Chem. 1997; 272:31725–31729.

Heart Protection Study Collaborative Group, The effects of cholesterol lowering with simvastatin on cause–specific mortality and on cancer incidence in 20,536 high–risk people: a randomized placebo–controlled trial BMC Medicine 2005; 3:6 (pp. 1–21).

MRC/BHF Heart Protection Study Collaborative Group, MRC/BHF Heart Protection Study of cholesterol–lowering therapy and of antioxidant vitamin supplementation in a wide range of patients at increased risk of coronary heart disease death: early safety and efficacy experience, Euro Heart J 1999; 20:725–741.

Armitage, Jane, Need for large scale randomized evidence about lowering LDL cholesterol in people with diabetes mellitus: MRC/BHF heart protection study and other major trials, Heart 2000; 84:357–360.

Ridker, Paul M., Number Needed to Treat With Rosuvastatin to Prevent First Cardiovascular Events and Death Among Men and Woman With Low Low–Density Lipoprotein Cholesterol and Elevated High–Sensitivity C–Reactive Protein: Justification for the Use of statins in Prevention: an Intervention Trial Evaluating Rosuvastatin (JUPITER), Circ Cardiovasc Qual Outcomes 2009; 1–8.

Goldberg, Ronald B., Cardiovascular Events and their Reduction With Pravastatin in Diabetic and Glucose–Intolerant Myocardial Infarction Survivors With Average Cholesterol Levels: Subgroup Analyses in the Cholesterol And Recurrent Events (CARE) Trial, Circulation 1998; 96:2513–2519.

Shepherd, James, Pravastatin in elderly individuals at risk of vascular disease (PROSPER): a randomized controlled trial, Lancet 2002; 360:1623–1630.

Sever, Peter S., Prevention of coronary and stroke events with atorvastatin in hypertensive patients who have average or lower–than–average cholesterol concentrations, in the Anglo–Scandinavian Cardiac Outcomes Trial–Lipid Lowering Arm (ASCOT–LLA): a multicentre randomized controlled trial, Lancet 2003; 361:1149–1158.

Colhoun, Helen M. Primary prevention of cardiovascular disease with atorvastatin in type 2 diabetes in the Collaborative Atorvastatin Diabetes Study (CARDS): multicentre randomized placebo–controlled trial, Lancet 2004; 364:685–696.

Briguori, Carlo, Novel Approaches for Preventing or Limiting Events (Naples) II Trial: Impact of a Single High Loading Dose of Atorvastatin on Periprocedural Myocardial Infarction, J. Am. Coll. Cardiol. 2009; 54:2157–2163.

Di Sciascio, Germano, Efficacy of Atorvastatin Reload in Patients on Chronic Statin Therapy Undergoing Percutaneous Coronary Intervention: Results of the ARMYDA–RECAPTURE (Atorvastatin for Reduction of Myocardial Damage during Angioplasty) Randomized Trial, J. Am. Coll. Cardiol. 2009; 54:558–565.

Ridker, Paul M., Rosuvastatin to Prevent Vascular Events in Men and Women with Elevated C–Reactive Protein, N Engl J Med 2008; 359(21):2195–2207.

Rikitake, Yoshiyuki, Rho GTPases, Statins, and Nitric Oxide, Circ Res 2005; 97:1232–1235.

Kjekshus, John, A statin in the treatment of heart failure? Controlled rosuvastatin multinational study in heart failure (CORONA): Study design and baseline characteristics, Euro J heart Failur 2005; 7:1059–1069.

Ford, Ian, Long–Term Follow–up of the West of Scotland Coronary Prevention Study, N Eng J Med 2007; 357(15):1477–1486.

Collaborative Atorvastatin Diabetes Study (CARDS), Baylor College of Medicine, Houston, TX, pp. 1–5.

Downs, John R., Primary Prevention of Acute Coronary Events With Lovastatin in Men and Women With Average Cholesterol Levels: Results of AFCAPS/TexCAPS, JAMA 1998; 279(20):1615–1622.

Correspondence—Comments on the MRC/BHF Heart Protection Study, Lancet 2003; 362:744–746.

Spatz, Erica S., From Here to Jupiter: Identifying New Patients for Statin Therapy Using Data From the 1999 2004 National Health and Nutrition Examination Survey, Circ Cardiovasc Qual Outcomes 2009:2;41–48.

Steiberg, Helmut O., Endothelial Dysfunction Is Associated With Cholesterol Levels in the High Normal Range in Humans, Circulation 1997; 96:3287–3293.

Dupuis,Jocelyn, Cholesterol Reduction rapidly Improves Endothelial Function After Acute Coronary Syndormes: The RECIFE (Reduction of Cholesterol in Ischemia and Function of the Eridothelium) Trial, Circulation 1999; 99:3227–3233.

Pedersen, Terje R., High–Dose Atorvastatin vs Usual–Dose Simvastatin for Secondary Prevention After Myocardial Infarction: The IDEAL Study: A Randomized Controlled Trial, JAMA 2005; 294(19):2437–2445.

Crouse, John R, III. Effect of Rosuvastatin on Progression of Carotid Intima–Media Thickness in Low–Risk individuals with subclinical Atherosclerosis, The METEOR Trial, JAMA 2007; 297(12):1344–1353.

Ridker, Paul M., The Editor's Roundtable: The JUPITER Trial—Initial Results and Clinical Implications, Am J. Cardiol 2009; 103:1417–1425.

Ridker, Paul M., The JUPITER Trial: Results, Controversies, and Implications for Prevention, Circ Cardiovasc Qual Outcomes 2009; 2:279–285.

Ridker, Paul M., Established and Emerging Plasma Biomarkers in the Prediction of First Atherothrombotic Events, Circulation 2004; 109:IV–6–IV–19.

Ridker, Paul M., Reduction in C–reactive protein and LDL cholesterol and cardiovascular event rates after initiation of rosuvastatin: a prospective study of the JUPITER trial, Lancet 2009; 373:1175–1182.

Ridker, Paul M., Comparison of C–Reactive Protein and Low–Density Lipoprotein Cholesterol Levels in the Prediction of First Cardiovascular Events, N Engl J Med 2002; 347(20):1557–1565.

Ridker, Paul, M., C–Reactive Protein Levels and Outcomes after Statin Therapy, N Engl J Med 2005; 352(1):20–28.

Stampfer, Meir J., Risk Factor Criteria, Circulation 2004; 109:IV–3–IV–5.

Willerson, James T., Inflammation as a Cardiovascular Risk Factor, Circulation 2004; 109:11–2–11010.

Wolfrum, Sebastian, Endothelium–Dependent Effects of Statins, Arterioscler Thromb Vasc Bio 2003; 23:729–736.

Clearfield, Michael, Air Force/Texas Coronary Atherosclerosis Prevention Study (AFCAPS/Tex CAPS): Efficacy and Tolerability of Long–Term Treatment with Lovastatin in Woman, J Women's Health Gender–Based Med 2001; 10 (10):971–981.

Rohde, Luis E.P., Survey of C–Reactive Protein and Cardiovascular Risk Factors in Apparently Health Men, Am J Cardiol 1999; 84:1018–1022.

Everett, Brendan M., Rosuvastatin in the Prevention of Stroke Among Men and Women With Elevated Levels of C–Reactive Protein: Justification for the Use of Statins in Prevention: An Intervention Trial Evaluating Rosuvastatin (JUPITER), Circulation 2010; 121:143–150.

Downs, John R., Design & Rationale of the Air Force/Texas Coronary Atherosclerosis Prevention Study (AFCAPS/Tex-CAPS), Am J Cardiol 1997; 80:287–293.

Ridker, Paul M., Measurement Of C–Reactive Protein For The Targeting Of Statin Therapy In The Primary Prevention Of Acute Coronary Events, N Eng J Med 2001; 344(26):1959–1965.

Bailey, Biguanides and NIDDM, Diabetes Care, 15:755–72 (1992).

Brown and Goldstein, A receptor–mediated pathway for cholesterol homeostasis, Science, 232(4746):34–47 (1986).

Chen, et al., More direct evidence for a malonyl–CoA–carnitine palmitoyltransferase I Interaction as a key event in pancreatic beta–cell signaling, Diabetes 43, 878–883 (1994).

Clissold, et al., Acarbose: A preliminary review of its pharmacodynamic and pharmacokinetic properties, and therapeutic potential, Drugs, 35:214–23 (1988).

Hulin et al., The glitazone family of antidiabetic agents, Current PharmaceuticalDesign, 2(1):85–102 (1996).

Inoguchi, et al., Preferential elevation of protein kinase C isoform beta II and diacylglycerol levels in the aorta and heart of diabetic rats: differential reversibility to glycemic control by islet cell transplantation, Proc. Natl Acad Sci USA, 89: II 059–11 063 (1992).

Ishii et al., Amelioration of vascular dysfunction in diabetic rats by an oral PKC beta inhibitor, Science, 272 (5262):728–731 (1996).

Kim, Regulation of mammalian acetyl–coenzyme A carboxylase, Annu. Rev. Nutr. 17:77–99 (1997).

McGarry and Brown, The mitochondrial carnitine palmitoyltransferase system. From concept to molecular analysis, Eur. J Biochem. 244, 1–14 (1997).

McGarry, et al., Regulation of ketogenesis and the renaissance of camitine palmitoyltransferase, Diebetes Metabol. Revs., 5, 271–284 (1989).

Mital, et al., Simvastatin upregulates Coronary vascular endothelial nitric oxide production in conscious dogs, Am J Physiol Heart Circ Physiol., 279(6):H2649–57 (2000).

Seema, et al., Simvastatin Acts Synergistically with ACE Inhibitors or Amlodipine to Decrease Oxygen Consumption in Rat Hearts, J Cardio. Pharm. 36(2):248–254 (2000).

Trochu, et al., Preservation of NO production by statins in the treatment of heart failure, Cardiovasc Res., 60(2):250–8 (2003).

Kaesemeyer WH., Holding smokers accountable for heart disease costs, Circulation. Aug. 1994;90(2)1029–32.

Kaesemeyer WH., Survival after congestive heart failure in Framingham Heart Study subjects, Circulation. Jan. 1994;89(1):506–7.

Kaesemeyer W, et al., Nitrates supplemented with L–arginine for the reversal and treatment of nitrate tolerance: Two case reports. Appl. Cardiopul. Pathophysiol., 6, 255–262, 1997.

Schror, K., et al., Generation of nitric oxide from organic nitrovasodilators during passage through the coronary vascular bed and its role in coronary vasodilation and nitrate tolerance. Blood Vessels. 28(1–2):62–66, 1991 (abstract only).

Iwaarden et al. 1992. What we can learn from the effects of thiol reagents on transport proteins. Biochemica et Biophysica acta. 1113: 161–170 (Summary Only).

Randomski et al. 1987. The anti–aggregating properties of vascular endothelium: Interactions between prostacyclin and nitric oxide. Br J Pharmacol. 92(3):639–46.

Van Buren et al. 1992. Estrogen–induced uterine vasodoliation is antagonized by L–nitroarginine methyl ester, an inhibitor of nitric oxide synthesis. Am J Obstet Gynecol. 167:826–33.

Lowe and Rubin. 1992. The pharmacological management of hypertension in prenancy. J Hypertension 10:201–207.

Chaves et al. 1993. Possible involvement of nitric oxide in estrogen–induced uterine edema in the immature rat. Brazilian J Med Biol Res 26:853–857.

Chung & Fung. 1993. Relationship Between Nitroglycerin–Induced Vascular Relaxation and Nitric Oxide Production: Probes with Inhibitors and Tolerance Development. Biochemical Pharmacology 45(1):157–163.

Byington et al. 1995. Pravastatin, Lipids, and Atherosclerosis in the Carotid Arteries (PLAC–II). Am J Cardio 76: Sept 28.:54C–59C.

Hamon et al. 1994. Long–Term Oral Administration of L–Arginine Reduces Intimal Thickening and Enhances Neoendothelium–Dependent Acetylcholine–Induced Relaxation After Arterial Injury. Circulation. 90:1357–1362.

Mollace et al. 1991. Evidence that L–argine possesses proconvulsant effects mediated through nitric oxide. NeuroReport 2(5):269–272. (abstract).

Thiemermann et al. 1991. Inhibition of the release of endothelium–derived relaxing factor in vitro and in vivo by dipeptides containing $N^G$–nitro–L–arginine. Br. J Pharma. 104:31–38.

Hecker et al. 1991. On the substrate specificity of nitric oxide synthase. FEBS Letters. 294(3):221–224.

Van Vliet et al. 1995. Different effects of 3–hydroxy–3–methyglutaryl–coenzyme A reductase inhibitors on sterol synthesis in various human cell types. Biochemica et Biophysica Acta. 1254:105–111.

Lamas et al. 1997. Regulation of Endothelial NO Synthase (NOS3) Expression in Situations of Vascular Injury. Meth Find Exp Clin Phrmacol. 19 (Suppl. A): 13–15.

McNamara et al. Biochemical Biophysical Res Comm. 1993. L–Arginine Inhibits Balloon Catheter–Induced Intimal Hyperplasia. 193(1):291–296.

Block et al. 1995. Hypoxia Inhibits L–argine uptake by pulmonary artery endothelial cells. Am. J Physiol Endocrinol Metab. 269:L574–L580.

Expert Panel on Detection, Evaluation, and Treatment of High Blood Cholesterol in Adults, Executive Summary of the 3rd Report of the National Cholesterol Education Program (NCEP) Expert Panel on Detection, Evaluation, and Treatment of High Blood Cholesterol in Adults (Adult Treatment Panel III), 2001.

Tanner et al. 1991. Oxidized Low Density Lipoproteins Inhibit Relaxations of Porcine Coronary Arteries: Role of Scavenger Receptor and Endothelium–Derived Nitric Oxide. Circulation. 83:2012–2020.

Erley, C.M., et al. 1993. Anti hypertensive Drugs in Rat Model Hypertension Induced by Chronic Endothelial derived Relaxing Factor (EDRF) Blockade, Hypertension. 22 (3): 437 (Abstract) P79.

Tojo et al. Effects of antihypertensive drugs on nitric oxide synthase activity in rat kidney. Kidney Int. 1996. vol. 49 (suppl 55):S–138–S–140.

Moritoki et al. Possible Involvement of Tyrosine, Kinase in the LPS–Promoted Initiation of L–Arginine–Induced Relaxation of Rat Aorta Mediated by Induction of No Synthase. 1995. Life Sciences. 57(11):125–130.

Stier et al. 1991. Dietary arginine fails to protect against cerebrovascular damage in stroke–prone hypertensive rats. Brain Res. vol. 549(2): 354–356 (Abstract only).

Conte et al. 1993. Press–coated tablets for time–programmed release of drugs. Biomaterials. vol. 14(13): 1017–1023.

Keith et al. 1982. Vascular tolerance to nitroglycerin and cyclic GMP generation in rat aortic smooth muscle. Pharmacol. Exp Thera. vol. 221(3):525–531 (Abstract Only).

Ignarro et al. 1989. Basic Polyamino Acids Rich in Arginine, Lysine, or Omithine Cause Both Enhancement of and Refractoriness to Formation of Endothelium–Derived Nitric Oxide in Pulmonary Artery and Vein. Circulation Res. 64:315–329.

Carey et al. 1987. An Arginine–Deficient Diet in Humans Does Not Evoke Hyperammonemia or Orotic Aciduria. J Nutr. 117:1734–1739.

Castana et al. 1993. Pharmacokinetic Study of the Relative Bioavailability and Bioequivalence After Oral Intensive or Repeated Short Term Treatment with Two Polyamino Acid Formulations. Int J Clin Pharma Res. XIII(2):93–105.

Sun et al. 1994. Pharmacokenetic Interaction Study Between Benazepril and Amlodipine in Healthy–Subjects. Eur. J Clin Pharma. vol. 47(3):285–289 (Abstract only).

Ashton et al. 1997. Altered $Na^+$–channel function as an in vitro model of the ischemic prenumbra: action of lubeluzole and other neuroprotective drugs. Brain Res. 745:210–221.

Bode–Boger et al. 1994. L–Arginine infusion decreases peripheral arterial resistance and inhibits platelet aggregation in healthy subjects. Clin Sci. 87:303–310.

Reutens et al. 1997. L–Arginine Infusion Increases Basal but not Activated Cerebral Blood Flow in Humans. J Cerebral Blood Flow Metabol. 17:309–315.

Creager et al. 1992. L–Arginine Improves Endothelium–dependent Vasodilation in Hypercholesterolemic Humans. J Clin, Investi. 90:1248–1253.

Bode–Boger et al. 1996. L–Arginine Induces Nitric Oxide–Dependent Vasodilation in Patients with Critical Limb Ischemia. Circulation 93:85–90.

Mayhan WG. 1996. Role of nitric oxide in histamine–induced increases in permeability of the blood–brain barrier. Brain Res. 743:70–76.

Morikawa et al. 1992. L–Arginine dilates rat pital arterioles by nitric oxide–dependent mechanisms and increases blood flow during focal cerabral ischaemia. Br. J Pharma. 107:905–907.

Myslivecek et al. 1997. Interactions between nitric oxide and dopamine in inhibitory learning and memory in newborn rate. Neuroscience. 79(3):659–669. (Abstract Only).

Steiner et al. 1984. Hyperinsulinemia and in vivo very–low–density lipoprotein–triglyceride kinetics. Am J. Physiol. 246(2 pt 1) E187–E192.

Pearson and Shaw 1982. Cardiovascular Disease, Its Prevention or Amelioration: Atherosclerosis. Chpt 16, 17, 20. pp. 307–320, 344, 245, 477, 735 and 835.

Saha et al. 1996. Effects of Acute and Chronic Inhibition of Nitric Oxide Synthase on Brown Adipose Tissue Thermogenesis. Jpn J Physiol. 46(5):375–82.

Blankenhorn et al. 1993. Coronary Angiographic Changes with Lovastatin Therapy: The Monitored Atherosclerosis Regression Study (MARS). Ann Intern Med 119(10):969–976.

Kaul, S. et al. By Jove! What Is a Clinician to Make of Jupiter? Arch Intern Med vol. 170, No. 12), Jun. 28, 2010.

Ridker et al. Relation of baseline high–sensitivity C–reactive protein level to cardiovascular outcomes with rosuvastatin in the justification for use of statins in prevention: an intervention trial evaluating rosuvastatin (Jupiter). Am J Cardiol. 106: 204–209, 2010.

Pitt et al., Pravastatin limitation of atherosclerosis in the coronary arteries (PLAC I): Reduction in atherosclerosis progression and clinical events. JACC vol. 26, No. 5 1133–1139, 1995.

Waters et al., Effects of cholesterol lowering on the progression of coronary atherosclerosis in women: a Canadian coronary atherosclerosis intervention trial (CCAIT) substudy.

Salonen, et al., Kuopio atherosclerosis prevention study (KAPS): a population–based primary preventive trial of the effect of LDL lowering on atherosclerotic progression in carotid and femoral arteries. Circulation vol. 92(7) 1758–1764, 1995.

Byington et al., Reduction in cardiovascular events during pravastatin therapy: pooled analysis of clinical events of the pravastatin atherosclerosis intervention program. Circulation 92(9) 2419–2425, 1995.

Waters, et al., Effects of monotherapy with an HMG–CoA reductase inhibitor on the progression of coronary atherosclerosis as assessed by serial quantitative arteriography, Circulation, 89; 959–968, 1984.

Crouse, J., et al., Pravastalin, lipids and atherosclerosis in the carotid arteries (PLAC–II), Am J Cardiol., 75: 455–459, 1995.

Brown, B., et al., Types of change in coronary stenosis severity and their relative importance in overall progression and regression of coronary disease. Observations form the FATS trial, Ann NY Acad Sci, 748: 407–418, 1994.

Stewart, F., et al., Benefits of lipid–lowering therapy in men with elevated apolipoprotein B are not confined to those with very high low density lipoprotein cholesterol, LACC 23(4) 899–906, 1994.

Rosuvastatin (Crestor) Label, 2010.
Pitavastatin (Livalo) Label, Jul. 30, 2009.
Atorvastatin (CADUET) Tablet Label, May 2009.
Atorvastatin (Lipitor) Tablet Label, Jun. 2006.
Atorvastatin (CADUET) Tablet Label, Apr. 2006.
Cervastatin (Lipobay) Label, 2001.
Cervastatin (Baycol) Label, 2001.
Atorvastatin (Lipitor) Label, 2001.
Fluvastatin (Lescol) Label, 2000.
Fluvastatin (Lescol) Label, 2001.
Lovastatin (Mevacor) Label, 2002.
Pravastatin (Pravachol) Label, 2002.
Rosuvastatin (Crestor) Label, 2003.

Simvastatin (Zocor) Label, 2002.

Gemfibrozil (Lopid) Label, 2003.

Simvastatin+Ezetimibe (Vytorin) Label, Sep. 2007.

Simvastatin+Niacin Extended–release (Simcor) Label, Jul. 2008.

Patent Term Extension Application of Re. 37, 314 (Reissue of U.S. patent No. 5,260,440) and Exhibits attached therewith, Hirai et al., Oct. 10, 2003.

Shimako Oishi et al. 2000. Atorvastatin (CI–)981 Clinical Pharmacokinetic Study. VII. Lack of Pharmacokinetic Interactions Between Atorvastatin and Nifedipine In Healthy Make Volunteers. Japanese Pharmacology & Therapeutics. vol. 28, No. 6, pp. 535–555 (Abstract Only).

Laufs et al. 2002. Rosuvastatin, a new HMG–CoA reductase inhibitor, upregulates endothelial nitric oxide synthase and protects from ischemic stroke in mice. *Brain Research.* vol. 942, Issue 1–2, Jun. 28, 2002, pp. 23–30.

Charles Rackley. 2002. Role of Statin Drugs in Acute Coronary Syndromes. *Current Atheroscleosis Reports*. 4:161–163.

Kaesemeyer WH. *Treatment with a Perfluorochemical Oxygen–Transport Fluid.* New England Journal of Medicine. 1982;307:1643.

Kaesemeyer WH, Prisant ML, Carr AA, *Verapamil and Nifedipine in Combination for the Treatment of Hypertensive Heart Disease.* American Journal of Hypertension. 1991;4:10.866–867.

Prisant LM. et al. *Nifedipine GITS Bezoar Archives Internal Medicine.* 1991;151:1868–1869.

Kaesemeyer WH, Carr AA, Bottini PB, Prisant LM. *Verapamil and Nifedipine in Combination for the Treatment of Hypertension.* J. Clin. Pharm. 1992;32:8.744.

Abou–Mohamed G, Kaesemeyer WH, Papapetropoulos A, Catravas JD, Caldwell RW. *Nitroglycerin (NTG) but not sodium nitroprusside (SNP), increases aortic ring cGMP levels Via an L–arginine dependent and L–NAME sensitive pathway.* FASEB J. 1995;9:A327 (abstract 1896).

Bottini PB, Carr AA, Kaesemeyer WH. *Variability in Lipid Measurements.* Amer. J. Hyperten. 1995;8:4 part 2.91A (abstract 637).

Abou–Mohamed G, Kaesemeyer WH, Papapetropoulos A, Catravas JD, Caldwell RW. *Nitroglycerin (NTG) but not sodium nitroprusside (SNP), increases aortic ring cGMP levels Via an L–arginine dependent and L–NAME sensitive pathway.* J. Am. Coll. Card. 1996;27:105A (abstract 917–119).

Ulrich D, Kaesemeyer WH, Kling JM, Caldwell RW. *L–arginine (LA) Reverses Cardiac Dysfunction Seen with Ischemia and Reperfusion (I&R) Following Chronic Angiotension Coverting Enzyme (ACE) Inhibition.* The Pharmacologist. 1997;39:1,49(abstract 156).

Kaesemeyer WH, Caldwell RB, Taylor TA, Huang J. Caldwell RW. *Pravastatin Activates Endothelial Nitric Oxide Synthase Independent of its Lipid Lowering Actions.* J. Am. Coll. Card. 1998;31:2 53A (abstract 801–1).

Kaesemeyer WH, Caldwell RB, Huang J. Caldwell RW. *Pravastatin Activates Endothelial Nitric Oxide Synthase Independent of its Cholesterol–Lowering Actions.* J. Am. Coll. Card. 1999;33:1 234–41.

Ogonowski AA, Kaesemeyer WH, Jin L, Ganapathy V, Leibach FH, Caldwell, RW. Effects of NO donors and synthase agonists on endothelial cell uptake of L–Arginine and superoxide production.Am J Physiol (CellPhysiol). 2000;278:1, C136–43.

Abou–Mohamed G, Kaesemeyer WH, Caldwell RB, Caldwell RW. Role of L–arginine in the vascular actions of and the development of tolerance to nitroglcerin. Br J Pharmacol. 2000;130:2,211–8.

Kaesemeyer WH, Caldwell RW. Atherosclerosis and nitric oxide. Circulation.2000;102:11,E90.

Kaesemeyer WH, Ogonowski AA, Jin L, Caldwell RB, Caldwell, RW.Endothelial nitric oxide synthase is a site of superoxide synthesis in endothelial cells treated with glyceryl trinitrateBr. J Pharmacol.2000;131:5, 1019–23.

Parker JO, Parker JD, Caldwell RW, Farrell B, Kaesemeyer WH.The effect of supplemental L–arginine on tolerance development during continuous transdermal nitroglycerin therapy. J Am Coll Cardiol.2002;39:7,1199–1203.

Stokes GS, Barin ES, Gilfilian KL, Kaesemeyer WH, Interactions of L–arginine, Isosorbide mononitrate, and angiotensin II inhibitors on arterial pulse wave. Am J Hypertens. 2003; 16: 9 pt 1, 719–24.

Abou–Mohamed G, Johnson JA, Jin L, El–Remessy AB, Do K, Kaesemeyer WH, Caldwell RB, Caldwell RB. Roles of superoxide, peroxynitrite, and protein kinase C in the development of tolerance to nitroglycerin. J Pharmacol Exp Ther. 2004;308: 1,289–299.

Dey A, Maric C, Kaesemeyer WH, Zaharis CZ, Stewart J, Pollock JS, Imig JD. Rofecoxib decreases renal injury in obese Zuker rats. Clin Sci. 2004; 107:6, 561–70.

Kaesemeyer WH, Jin L, Caldwell RB, Caldwell RW. Role of Oxidative Stress in Endothelial Cell Dysfunction. In: Biomedical Significance of Nitric Oxide, Stefano GB(editor). Medical Science International Ltd. Warsaw–New York, 2003, p. 139–151.

Kaesemeyer W. Statin drug eluting stent (DES) for early stent thrombosis. Atherosclerosis. 2009; 207: 2, 343.

R. Datar, W.H. Kaesemeyer, S. Chandra, D. J. Fulton, R. W. Caldwell Acute activation of eNOS by statins involves scavenger receptor B–1, G protein subunit Gi, Phospholipase C and calcium influx. British Journal of Pharmacology. 2010; 160: 1765–1772.

Abou–Mohamed G, Kaesemeyer WH, Caldwell RW. Comparison of tolerance to isosorbide mononitrate (ISMN) vs glyceryl trinitrate (GTN). *FASEB J.* 2004;18:(5 part II):A983–A984 (abstract 643.12).

Datar R, Kaesemeyer WH, Fulton DJ, Caldwell RW. Acute Activation of eNOS by Lovastatin Involves Scavenger Receptor–B1. Circulation. 2008; 118:S__277 (abstract 237).

Kaesemeyer, et al. *Verapamil and nifedipine* in combination for the treatment of hypertension. *J Clin Pharmacol* 1994. 34:48–51.

Lee et al. Cost–Effectiveness of Using High–Sensitivity C–Reactive Protein to Identify Intermediate–and Low–Cardiovascular–Risk Individuals for Statin Therapy. *Circulation*. 2010; 122:1478–1487.

Grundy et al. Implications of Recent Clinical Trials for the National Cholesterol Education Program Adult Treatment Panel III Guidelines. *Circulation*. 2004;110:227–239.

Mary Dunne Roberts. Crestor (Rosuvastatin calcium) NDA 21–366 Jupiter, FDA Presentation Slides pp. 1–14, Endocrinologic and Metabolic Drugs Advisory Committee Meeting, Gaithersburg, MD. Dec. 15, 2009.

Transcript of Dec. 15, 2009 FDA meeting and Index. Department of Health and Human Services United States Food and Drug Administration Center for Drug Evaluation and Research. Paper Mill Reporting. pp. 1–324, Index Sheet 1–33. Endocrinologic and Metabolic Drugs Advisory Committee Meeting. Gaithersburg, MD. Dec. 15, 2009.

Annunzio et al. Rosuvastatin Given During Reperfusion Decreases Infarct Size and Inhibits Matrix Metalloproteinase–2 Activity in Normocholesterolemic andHypercholesterolemic Rabbits. *Cardiovasc Pharmacol.* vol. 53, No. 2, Feb. 2009.

Calvert & Lefer. Statin therapy and myocardial no–reflow. *British journal of Pharmacology* (2006) 149 229–231.

National Institute of Health. Detection, Evaluation, and Treatment of High Blood Cholesterol in Adults (Adult Treatment Panel III), Final Report. National Cholesterol Education Program, National Heart, Lung, and Blood Institute, National Institutes of Health, *NIH Publication* No. 02–5215. pp. I–1 to V–5. Sep. 2002. ATP III.

Baron et al. A Randomized Trial of Aspirin to Prevent Colorectal Adenomas. *N Engl J Med* 2003;348:891–9.

Zhao et al. Pretreatment with simvastatin reduces myocardial no–reflow by opening mitochondrial $K_{ATP}$ channel. *British Journal of Pharmacology* (2006) 149, 243–249.

Ludman et al. Statins and cardioprotection—More than just lipid lowering? *Pharmacology & Therapeutics* 122 (2009) 30–43.

Atorvastatin Calcium (Lipitor) Label, Jun. 2009.

Rosuvastatin Calcium (Crestor) Label, Jun. 2010.

Rosuvastatin (Crestor) to reduce the risk of major CV events. Presentation slides CC1–CC108, including slides of Dr. Paul M. Ridker. Endocrinologic and Metabolic Drugs Advisory Committee Meeting, Gaithersburg, MD. Dec. 15, 2009.

LaRosa JC, Grundy SM, Waters DD, et al. for the Treating to New Targets (TNT) Investigators. Intensive lowering with atorvastatin in patients with stable Coronary disease. N Engl J Med. 2005;352: 1425–1435.

Pierre Amarenco, et al. for the SPARCL Investigators. Results of the Stroke Prevention by Aggressive Reduction in Cholesterol Levels (SPARCL)Trial by Stroke Subtypes. *Stroke.* 2009;40:1405–1409.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1 and 3-6 are determined to be patentable as amended.

Claims 7-14, dependent on an amended claim, are determined to be patentable.

New claims 15-20 are added and determined to be patentable.

1. A method for treating a *nonhyperlipidemic* subject who would benefit from increased Nitric Oxide production in a tissue comprising:
administering to the *nonhyperlipidemic* subject in need of such treatment [, irrespective of the subject's cholesterol level,] a Hmg-CoA reductase inhibitor in an amount effective to increase Nitric Oxide production in said tissue of the subject.

3. The method of claim [2] *1*, wherein said amount is sufficient to increase Nitric Oxide production above normal baseline levels.

4. The method of claim [2] *1*, wherein the subject has a cytokine-induced condition comprising an abnormally low level of nitric oxide synthase activity.

5. The method of claim [2] *1*, wherein the subject has an abnormally elevated risk of pulmonary hypertension.

6. The method of claim [2] *1*, wherein the subject has pulmonary hypertension.

*15. The method of claim 1, wherein the treatment reduces the risk of stroke in the subject.*

*16. The method of claim 1, wherein the treatment reduces the risk of angina in the subject.*

*17. The method of claim 1, wherein the treatment reduces the risk of reperfusion injury in the subject.*

*18. The method of claim 15, wherein the subject is selected on a basis of having hypertension.*

*19. The method of claim 16, wherein the subject is selected on a basis of having hypertension.*

*20. The method of claim 17, wherein the subject is selected on a basis of having hypertension.*

\* \* \* \* \*